(12) United States Patent
Cantor-Balan et al.

(10) Patent No.: US 11,744,641 B2
(45) Date of Patent: Sep. 5, 2023

(54) SYSTEMS AND METHODS FOR PULSING AND DIRECTING A PULSED LASER BEAM TO TREAT DENTAL TISSUE

(71) Applicant: Convergent Dental, Inc., Needham, MA (US)

(72) Inventors: Roni Cantor-Balan, Natick, MA (US); William H. Groves, Jr., Arlington, MA (US); Charles H. Dresser, Arlington, MA (US); Nathan P. Monty, Shrewsbury, MA (US)

(73) Assignee: Convergent Dental, Inc., Needham, MA (US)

( * ) Notice: Subject to any disclaimer, the term of this patent is extended or adjusted under 35 U.S.C. 154(b) by 390 days.

(21) Appl. No.: 16/821,263

(22) Filed: Mar. 17, 2020

(65) Prior Publication Data
US 2020/0337768 A1    Oct. 29, 2020

Related U.S. Application Data

(63) Continuation of application No. 15/587,525, filed on May 5, 2017, now Pat. No. 10,631,929.

(Continued)

(51) Int. Cl.
*A61B 18/20*   (2006.01)
*A61C 1/00*    (2006.01)
*A61B 18/00*   (2006.01)

(52) U.S. Cl.
CPC ............ *A61B 18/20* (2013.01); *A61C 1/0046* (2013.01); *A61B 2018/00321* (2013.01); *A61B 2018/00601* (2013.01)

(58) Field of Classification Search
None
See application file for complete search history.

(56) References Cited

U.S. PATENT DOCUMENTS

| 5,388,987 A | 2/1995 | Badoz et al. |
| 5,957,915 A | 9/1999 | Trost |

(Continued)

FOREIGN PATENT DOCUMENTS

| CA | 2620095 | 4/2007 |
| WO | 97/10768 | 3/1997 |

(Continued)

OTHER PUBLICATIONS

Chang K et al.,(2011) "Adhesion studies on dental enamel surfaces irradiated by a rapidly scanned carbon dioxide laser" Proc SPIE Int Soc Opt Eng., 1-10.

(Continued)

*Primary Examiner* — Ankit D Tejani
(74) *Attorney, Agent, or Firm* — Goodwin Procter LLP

(57) ABSTRACT

A laser beam treatment system that delivers laser beam pulses to a dental treatment area according to a particular pattern is described. In various instances, the spacing of the pattern (e.g., locations at which pulses are delivered and the distances therebetween) and/or the timing of the pattern (e.g., amount of time between the delivery of pulses to a first location and a later location that abuts the first location) can have a demonstrable effect on ablation performance. The effects can include, for example: improved ablation efficiency, improved surface smoothness, improved material removal rate, and/or the absence of melt, carbonization or other negative surface features.

6 Claims, 38 Drawing Sheets

Related U.S. Application Data

(60) Provisional application No. 62/332,586, filed on May 6, 2016.

(56) References Cited

U.S. PATENT DOCUMENTS

| | | | |
|---|---|---|---|
| 7,220,256 | B2 | 5/2007 | Hobart et al. |
| 8,029,501 | B2 | 10/2011 | Miller |
| 8,276,592 | B2 | 10/2012 | Davenport et al. |
| 2006/0189965 | A1* | 8/2006 | Litvak .................. A61C 13/12 |
| | | | 433/29 |
| 2013/0059264 | A1 | 3/2013 | Monty |
| 2014/0030671 | A1 | 1/2014 | Awazu et al. |
| 2014/0363784 | A1* | 12/2014 | Monty ................. A61C 1/0007 |
| | | | 433/29 |
| 2015/0223911 | A1 | 8/2015 | Lukac et al. |
| 2015/0342703 | A1 | 12/2015 | Monty et al. |

FOREIGN PATENT DOCUMENTS

| | | |
|---|---|---|
| WO | WO-2004/006793 A1 | 1/2004 |
| WO | 2011/130231 | 10/2011 |
| WO | 2014/123904 A2 | 8/2014 |

OTHER PUBLICATIONS

Chan K et al.,(2014) "Analysis of enamel surface damage after selective laser ablation of composite from tooth surfaces," Photon Lasers Med; 3(1), 37-45.

Nguyen D et al,(2011) "High-speed scanning ablation of dental hard tissues with a I=9.3 mm $CO^2$ laser: Heat accumulation and peripheral thermal damage," J Biomed Opt, 16(7): 1-12.

Chan K et al.,(2011) "Rapid and selective removal of composite from tooth surfaces with a 9.3 mm $CO^2$ laser using spectral Feedback," Laser Surg Med.43(8): 824-32.

Chan K et al.,(2011) "Selective removal of dental composite using a rapidly scanned carbon dioxide laser," Proc Spie Int Soc Opt Eng; pp. 1-9.

Tao YC et al., (2008) "Selective removal of natural occlusal caries by coupling near-infrared imaging with a $CO^2$ laser," Proc SPIE Int Soc Opt Eng.; 6843; pp. 1-14.

International Search Report and Written Opinion of the International Searching Authority dated Oct. 2, 2017 for Application No. PCT/US2017/031194, filing date May 5, 2017.

Ertl, et al., "Hard Tissue Ablation With Pulsed CO2 Lasers", SPIE vol. 1800 pp. 176-181 (2015}.

Gerold K.H. Eyrich, "Laser-osteotomy induced changes in bone", Medical Laser Application 20 (2005) 25-36.

M. Frentzen, et al., "Osteotomy with 80 μs C02 laser pulses—histological results", Lasers Med Sci (2003)18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016. 1199743 (published online Jun. 27, 2016).

Ivanenko, et al., "Hard tissue ablation with sub-μs CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsugrical laser bone ablation," Int J CARS (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation,".

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

* cited by examiner

| Pattern | Grid Size | Pulse Width (uS) | Jump Delay (uS) | Number of Passes (-) | Power (W) | Cut Time (S) |
|---|---|---|---|---|---|---|
| DECAY-006, 410 | 3 x 3 | 60 | 1000 | 589 | 11.2 | 233 |
| SP125, 412 | 3 x 3 | 32.5 | 500 | 652 | 11.2 | 234 |

| Table 1 | |
|---|---|
| Variable | Input Value |
| Frequency [KHz] * | 1 |
| Mark Speed [mm/s] | 300 |
| Laser On delay [μs] | 0 |
| Laser Off delay [μs] | 0 |
| Mark delay [μs] | 10 |
| Poly delay [μs] | 0 |
| Focus (Z) offset [mm] | 0.00 |
| Jump speed [mm/s] | 1000.0 |
| Jump delay [μs] | 500 |
| Vari. Jump length [mm] | 0.00 |
| Vari. Jump delay [μs] | 0 |
| Wobble frequency [Hz] | 0 |
| Wobble width [mm] | 0.00 |
| # of pulses per location | 1 |
| Scaled Size in X-Axis [mm] | 0.74 |
| Scaled Size in Y-Axis [mm] | 0.84 |

* When the number of pulses per location is 1, the frequency variable is void but has to be input as a non-zero integer. For all SP patterns it is set to 1 KHz.

| Table 3 | |
|---|---|
| Variable | Input Value |
| Nominal Pattern Diameter [mm] | 1.25 +/- 0.15 |
| Nominal Pattern Area [mm$^2$] | 1.227 |
| Average point-to-point frequency within the pattern at Max PD [Hz] | 1232 |
| Average point-to-point frequency within the pattern at Min PD [Hz] | 1349 |
| Average Point Repeat Rate at Max PD [Hz] | 945 |
| Average Point Repeat Rate at Min PD [Hz] | 1019 |
| Max Average Power [W] | 26.2 |
| Min Average Power [W] | 2.9 |
| Max Irradiance [W/mm2] | 21.3 |
| Min Irradiance [W/mm2] | 2.4 |
| Max Pulse Energy [mJ] | 25.7 |
| Min Pulse Energy [mJ] | 2.8 |
| Max Peak Power [W] | 2570.6 |
| Min Peak Power [W] | 284.5 |
| Foot Pedal response | Linear |
| Mass Removal Rate in enamel [mg/sec]* | 1.27 |

| Table 2 | |
|---|---|
| Variable | Input Value |
| Max Pulse Duration | 90 |
| Min Pulse Duration | 1 (10 at 10% on the GUI) |
| Max Jump Delay [μs] | 10000 (at 10% on the GUI) |
| Min Jump Delay [μs] | 500 (at 100% on the GUI) |
| Max Mist [%] | 100 |
| Min Mist [%] | 70 |

FIG. 5B

| Table 1 ||
|---|---|
| Variable | Input Value |
| Frequency [KHz] * | 1 |
| Mark Speed [mm/s] | 300 |
| Laser On delay [µs] | 0 |
| Laser Off delay [µs] | 0 |
| Mark delay [µs] | 10 |
| Poly delay [µs] | 0 |
| Focus (Z) offset [mm] | 0.00 |
| Jump speed [mm/s] | 1000.0 |
| Jump delay [µs] | 1000 |
| Vari. Jump length [mm] | 0.00 |
| Vari. Jump delay [µs] | 0 |
| Wobble frequency [Hz] | 0 |
| Wobble width [mm] | 0.00 |
| # of pulses per location | 1 |
| Scaled Size in X-Axis [mm] | 0.41 |
| Scaled Size in Y-Axis [mm] | 0.56 |

| Table 2 ||
|---|---|
| Variable | Input Value |
| Max Pulse Duration [µs] | 130 |
| Min Pulse Duration [µs] | 1 (15 at 10% on the GUI) |
| Max Jump Delay [µs] | 10000 (at 10% on the GUI) |
| Min Jump Delay [µs] | 1000 (at 100% on the GUI) |
| Max Mist [%] | 100 |
| Min Mist [%] | 70 |

FIG. 6B

| Table 3 ||
|---|---|
| Variable | Input Value |
| Nominal Pattern Diameter [mm] | 1.00 +/- 0.15 |
| Nominal Pattern Area [mm$^2$] | 0.785 |
| Average point-to-point frequency within the pattern at Max PD [Hz] | 758 |
| Average point-to-point frequency within the pattern at Min PD [Hz] | 832 |
| Average Point Repeat Rate at Max PD [Hz] | 543 |
| Average Point Repeat Rate at Min PD [Hz] | 580 |
| Max Average Power [W] | 23.0 +/-20% |
| Min Average Power [W] | 1.7 +/-20% |
| Max Irradiance [W/mm2] | 28.6 |
| Min Irradiance [W/mm2] | 2.2 |
| Max Pulse Energy [mJ] | 42.4 |
| Min Pulse Energy [mJ] | 3.1 |
| Max Peak Power [W] | 325.8 |
| Min Peak Power [W] | 208.7 |
| Foot Pedal response | Linear |
| Mass Removal Rate in enamel [mg/sec]* | 1.5 |

| Table 1 | |
|---|---|
| Variable | Input Value |
| Frequency [KHz] * | 1 |
| Mark Speed [mm/s] | 300 |
| Laser On delay [μs] | 0 |
| Laser Off delay [μs] | 0 |
| Mark delay [μs] | 10 |
| Poly delay [μs] | 0 |
| Focus (Z) offset [mm] | 0.00 |
| Jump speed [mm/s] | 1000.0 |
| Jump delay [μs] | 2000 |
| Vari. Jump length [mm] | 0.00 |
| Vari. Jump delay [μs] | 0 |
| Wobble frequency [Hz] | 0 |
| Wobble width [mm] | 0.00 |
| # of pulses per location | 1 |
| Scaled Size in X-Axis [mm] | 0.31 |
| Scaled Size in Y-Axis [mm] | 0.38 |

| Table 2 | |
|---|---|
| Variable | Input Value |
| Max Pulse Duration [μs] | 130 |
| Min Pulse Duration [μs] | 1 (15 at 10% on the GUI) |
| Max Jump Delay [μs] | 10000 (at 10% on the GUI) |
| Min Jump Delay [μs] | 2000 (at 100% on the GUI) |
| Max Mist [%] | 100 |
| Min Mist [%] | 70 |

FIG. 7B

| Table 3 | |
|---|---|
| Variable | Input Value |
| Nominal Pattern Diameter [mm] | 0.75 |
| Nominal Pattern Area [mm$^2$] | 0.442 |
| Average point-to-point frequency within the pattern at Max PD [Hz] | 439 |
| Average point-to-point frequency within the pattern at Min PD [Hz] | 462 |
| Average Point Repeat Rate at Max PD [Hz] | 356 |
| Average Point Repeat Rate at Min PD [Hz] | 368 |
| Max Average Power [W] | 15.3 +/- 20% |
| Min Average Power [W] | 1.1 +/- 20% |
| Max Irradiance [W/mm2] | 34.6 |
| Min Irradiance [W/mm2] | 2.5 |
| Max Pulse Energy [mJ] | 43 |
| Min Pulse Energy [mJ] | 3.1 |
| Max Peak Power [W] | 330.5 |
| Min Peak Power [W] | 205.3 |
| Foot Pedal response | Linear |

| Table 1 ||
|---|---|
| Variable | Input Value |
| Frequency [KHz]* | 1 |
| Mark Speed [mm/s] | 300 |
| Laser On delay [µs] | 0 |
| Laser Off delay [µs] | 0 |
| Mark delay [µs] | 10 |
| Poly delay [µs] | 0 |
| Focus (Z) offset [mm] | 0.00 |
| Jump speed [mm/s] | 1000.0 |
| Jump delay [µs] | 2000 |
| Vari. Jump length [mm] | 0.00 |
| Vari. Jump delay [µs] | 0 |
| Wobble frequency [Hz] | 0 |
| Wobble width [mm] | 0.00 |
| # of pulses per location | 1 |
| Scaled Size in X-Axis [mm] | 0.22 |
| Scaled Size in Y-Axis [mm] | 0.31 |

| Table 2 ||
|---|---|
| Variable | Input Value |
| Max Pulse Duration [µs] | 130 |
| Min Pulse Duration [µs] | 1 (15 at 10% on the GUI) |
| Max Jump Delay [µs] | 10000 (at 10% on the GUI) |
| Min Jump Delay [µs] | 2000 (at 100% on the GUI) |
| Max Mist [%] | 100 |
| Min Mist [%] | 70 |

FIG. 8B

| Table 3 ||
|---|---|
| Variable | Input Value |
| Nominal Pattern Diameter [mm] | 0.50 |
| Nominal Pattern Area [mm$^2$] | 0.196 |
| Average point-to-point frequency within the pattern at Max PD [Hz] | 436 |
| Average point-to-point frequency within the pattern at Min PD [Hz] | 450 |
| Average Point Repeat Rate at Max PD [Hz] | 275 |
| Average Point Repeat Rate at Min PD [Hz] | 282 |
| Max Average Power [W] | 12 +/-20% |
| Min Average Power [W] | 0.8 +/- 20% |
| Max Irradiance [W/mm2] | 61.1 |
| Min Irradiance [W/mm2] | 4.1 |
| Max Pulse Energy [mJ] | 43.7 |
| Min Pulse Energy [mJ] | 2.9 |
| Max Peak Power [W] | 336 |
| Min Peak Power [W] | 190.9 |
| Foot Pedal response | Linear |

| Table 1 ||
|---|---|
| Variable | Input Value |
| Frequency [KHz] | 1 |
| Mark Speed [mm/s] | disabled |
| Laser On delay [μs] | disabled |
| Laser Off delay [μs] | disabled |
| Mark delay [μs] | disabled |
| Poly delay [μs] | disabled |
| Focus (Z) offset [mm] | 0.00 |
| Jump speed [mm/s] | 1000.0 |
| Jump delay [μs] | 0 |
| Vari. Jump length [mm] | 0.00 |
| Vari. Jump delay [μs] | 0 |
| Wobble frequency [Hz] | disabled |
| Wobble width [mm] | disabled |
| # of pulses per location | 1 |
| Size in X-Axis [mm] | NA |
| Size in Y-Axis [mm] | NA |

| Table 2 ||
|---|---|
| Variable | Input Value |
| Max Pulse Duration [μs] | 130 |
| Min Pulse Duration [μs] | 1 (15 at 10% on the GUI) |
| Max Jump Delay [μs] | 10000 (at 10% on the GUI) |
| Min Jump Delay [μs] | 0 (at 100% on the GUI) |
| Max Mist [%] | 100 |
| Min Mist [%] | 70 |

FIG. 9B

| Table 3 ||
|---|---|
| Variable | Input Value |
| Nominal Pattern Diameter [mm] | 0.25 |
| Nominal Pattern Area [mm²] | 0.049 |
| Average point-to-point frequency within the pattern at Max PD [Hz] | 71 |
| Average point-to-point frequency within the pattern at Min PD [Hz] | 71 |
| Average Point Repeat Rate at Max PD [Hz] | 71 |
| Average Point Repeat Rate at Min PD [Hz] | 71 |
| Max Average Power [W] | 3.2 |
| Min Average Power [W] | 0.2 |
| Max Irradiance [W/mm2] | 65.2 |
| Min Irradiance [W/mm2] | 4.1 |
| Max Pulse Energy [mJ] | 44.9 |
| Min Pulse Energy [mJ] | 2.8 |
| Max Peak Power [W] | 345.4 |
| Min Peak Power [W] | 185.5 |
| Foot Pedal response | Linear |
| Mass Removal Rate in enamel [mg/sec]* | 0.13 |

| Pulse Width (us) | Energy Per Pulse (mJ) | Fluence w/ 0.25mm Spot (J/cm^2) |
|---|---|---|
| 3 | 1.6 | 3.3 |
| 5 | 2.5 | 5.1 |
| 25 | 6.8 | 13.9 |
| 50 | 15.8 | 32.2 |
| 100 | 33 | 67.2 |
| 200 | 63 | 128.3 |
| 300 | 88 | 179.3 |
| 400 | 111 | 226.1 |
| 500 | 131 | 266.9 |

FIG. 11

1202 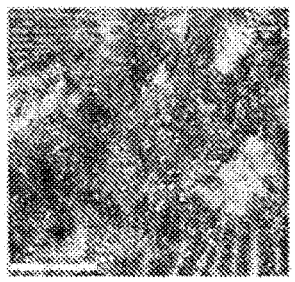 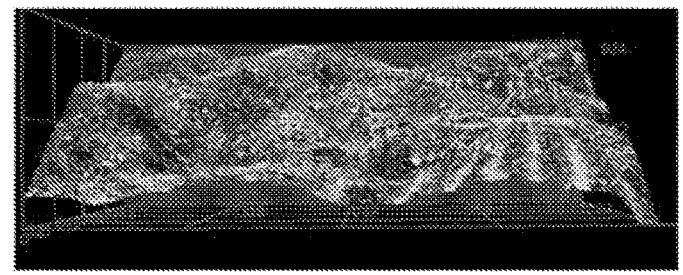
1204  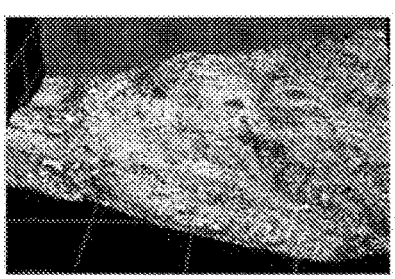
1206 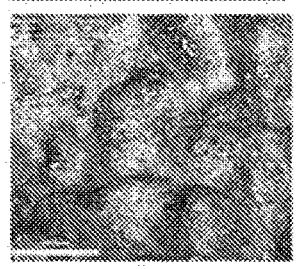 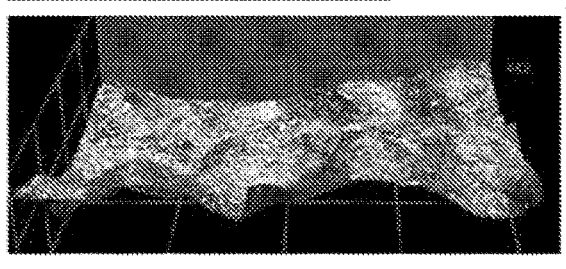
1208  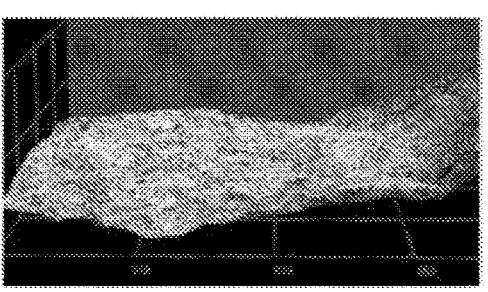
FIG. 12

| Single Pulse Pattern Parameters | SP1.25 | SP1.00 | SP0.75 | SP050 | SP0.25 |
|---|---|---|---|---|---|
| Nominal Pattern Diameter [mm] | 1.25 | 1.00 | 0.75 | 0.5 | 0.25 |
| Nominal Pattern Area [mm2] | 1.227 | 0.785 | 0.442 | 0.196 | 0.049 |
| Pulse Ontime MAX (width) [us] (100% foot pedal) | 90 | 130 | 130 | 130 | 130 |
| Pulse Ontime MIN (width) [us] (10% foot pedal) | 10 | 15 | 15 | 15 | 15 |
| Pulse Freq within the pattern at Max PD [Hz] | 1232 | 758 | 439 | 436 | 71 |
| Pulse Freq within the pattern at Min PD [Hz] | 1349 | 832 | 462 | 450 | 71 |
| First pulse to end of last pulse pattern time at MAX PD [seconds] | 0.0423 | 0.0306 | 0.0550 | 0.021 | NA |
| First pulse to end of last pulse pattern time at MIN PD [seconds] | 0.0382 | 0.0278 | 0.0525 | 0.020 | NA |
| MAX Average Power (at MAX PD) [W] | 23.8 | 20.7 | 13.8 | 10.9 | 2.8 |
| MIN Average Power (at MIN PD) [W] | 1.2 | 1.4 | 0.9 | 0.7 | 0.2 |
| Pulse Freq within pattern [Hz] | 1232 | 758 | 439 | 436 | 71 |
| Pulse Ontime(width) [us] | 90 | 130 | 130 | 130 | 130 |
| Pulses Per Point (per location) | 1 | 1 | 1 | 1 | 1 |
| Points (locations) per Pattern | 53 | 24 | 25 | 10 | 1 |
| Total Points Duration (all of the laser on-time for the pattern) | 0.00477 | 0.00312 | 0.00325 | 0.0013 | 0.00013 |
| First pulse to end of last pulse pattern time [seconds] | 0.0382 | 0.0306 | 0.055 | 0.021 | NA |
| Point to Point Delay+Jump time [seconds] | 0.000643 | 0.0011948 | 0.00215625 | 0.002189 | 0 |
| Last Delay+Pattern repeat Delay [seconds] | 0.0138 | 0.0136 | 0.0150 | 0.0148 | 0.0139 |
| Total Pattern Time (Time of All Packets & Delays) [seconds] | 0.0520 | 0.0442 | 0.0700 | 0.0358 | 0.0140 |
| Total Pattern Repeat Rate [Hz] | 19.23 | 22.62 | 14.29 | 27.93 | 71.28 |
| Average Point repeat rate (pattern repeat rate * # of points) [Hz] | 1019 | 543 | 357 | 279 | 71 |
| Ontime Percentage [%] | 9.17 | 7.06 | 4.64 | 3.63 | 0.93 |
| Equiv. Pulse Freq for the Pattern (considering the pattern repeat delay) [Hz] | 1019 | 543 | 357 | 279 | 71 |
| Average Power [W] | 23.8 | 19.2 | 14 | 10.8 | 2.8 |
| Pulse Energy [Jouls] (W_ave/freq.) | 0.0234 | 0.0354 | 0.0392 | 0.0387 | 0.0393 |
| Pulse Energy [mJ] | 23.4 | 35.4 | 39.2 | 38.7 | 39.3 |
| Peak Power [W] (energy joules/pulse duration) | 259.5 | 272.0 | 301.5 | 297.4 | 302.2 |

FIG. 13

| SP 0.75 | 50% FP, 2mS JD | | SP 1.00 | 60% FP, 1mS JD | | SP 1.25 | 40% FP, 0.5mS JD | |
|---|---|---|---|---|---|---|---|---|
| Sample D | | | Sample E | | | Sample F | | |
| ISO 25178 | | | ISO 25178 | | | ISO 25178 | | |
| Height Parameters | | | Height Parameters | | | Height Parameters | | |
| Sq | 8.67 | µm | Sq | 6.3 | µm | Sq | 9.9 | µm |
| Ssk | -0.195 | | Ssk | 0.195 | | Ssk | 0.556 | |
| Sku | 2.37 | | Sku | 3.06 | | Sku | 3.43 | |
| Sp | 41.6 | µm | Sp | 24.5 | µm | Sp | 41.9 | µm |
| Sv | 79.9 | µm | Sv | 21.7 | µm | Sv | 27.4 | µm |
| Sz | 122 | µm | Sz | 46.3 | µm | Sz | 69.3 | µm |
| Sa | 7.12 | µm | Sa | 5.02 | µm | Sa | 7.77 | µm |
| Hybrid Parameters | | | Hybrid Parameters | | | Hybrid Parameters | | |
| Sdq | 2.32 | | Sdq | 1.63 | | Sdq | 1.51 | |
| Sdr | 113 | % | Sdr | 75.6 | % | Sdr | 66.9 | % |
| ASME B46.1 3D Parameters | | | ASME B46.1 3D Parameters | | | ASME B46.1 3D Parameters | | |
| St | 122 | µm | St | 46.3 | µm | St | 69.3 | µm |

| XC 0.75 | 100% FP, 41uS PW | | XC 1.00 | 100% FP, 75uS PW | | XC 1.25 | 100% FP, 95uS PW | |
|---|---|---|---|---|---|---|---|---|
| Sample G | | | Sample H | | | Sample I | | |
| ISO 25178 | | | ISO 25178 | | | ISO 25178 | | |
| Height Parameters | | | Height Parameters | | | Height Parameters | | |
| Sq | 17.3 | µm | Sq | 48.4 | µm | Sq | 75.5 | µm |
| Ssk | -0.267 | | Ssk | -0.534 | | Ssk | -0.00667 | |
| Sku | 3.31 | | Sku | 3.13 | | Sku | 3.96 | |
| Sp | 50.1 | µm | Sp | 132 | µm | Sp | 267 | µm |
| Sv | 65.4 | µm | Sv | 161 | µm | Sv | 246 | µm |
| Sz | 116 | µm | Sz | 293 | µm | Sz | 512 | µm |
| Sa | 13.4 | µm | Sa | 38 | µm | Sa | 56.2 | µm |
| Hybrid Parameters | | | Hybrid Parameters | | | Hybrid Parameters | | |
| Sdq | 1.57 | | Sdq | 2.39 | | Sdq | 8.8 | |
| Sdr | 68.7 | % | Sdr | 117 | % | Sdr | 219 | % |
| ASME B46.1 3D Parameters | | | ASME B46.1 3D Parameters | | | ASME B46.1 3D Parameters | | |
| St | 116 | µm | St | 293 | µm | St | 512 | µm |

FIG. 14A

| SP 0.75 | 30% FP, 2mS JD | | SP 0.75 | 30% FP, 2mS JD | | SP 1.00 | 40% FP, 1mS JD | | SP 1.00 | 40% FP, 1mS JD | | SP 1.25 | 30% FP, 0.5mS JD | |
|---|---|---|---|---|---|---|---|---|---|---|---|---|---|---|
| Sample 4 | | | Sample 4 etch | | | Sample 5 | | | Sample 5 etch | | | Sample 6 | | |
| ISO 25178 | | | ISO 25178 | | | ISO 25178 | | | ISO 25178 | | | ISO 25178 | | |
| Height Parameters | | | Height Parameters | | | Height Parameters | | | Height Parameters | | | Height Parameters | | |
| Sq | 7.22 | μm | Sq | 6.35 | μm | Sq | 7.53 | μm | Sq | 8.39 | μm | Sq | 6.57 | μm |
| Ssk | 1.26 | | Ssk | -0.144 | | Ssk | 0.0897 | | Ssk | 0.0189 | | Ssk | 0.0654 | |
| Sku | 7.18 | | Sku | 2.92 | | Sku | 3.33 | | Sku | 3.02 | | Sku | 2.95 | |
| Sp | 51.7 | μm | Sp | 22.1 | μm | Sp | 31.4 | μm | Sp | 31.2 | μm | Sp | 26.7 | μm |
| Sv | 22.8 | μm | Sv | 27.5 | μm | Sv | 28.2 | μm | Sv | 34.6 | μm | Sv | 22.4 | μm |
| Sz | 74.5 | μm | Sz | 49.6 | μm | Sz | 59.6 | μm | Sz | 65.8 | μm | Sz | 49.1 | μm |
| Sa | 5.32 | μm | Sa | 5.11 | μm | Sa | 5.94 | μm | Sa | 6.6 | μm | Sa | 5.21 | μm |
| Hybrid Parameters | | | Hybrid Parameters | | | Hybrid Parameters | | | Hybrid Parameters | | | Hybrid Parameters | | |
| Sdq | 1.7 | | Sdq | 1.51 | | Sdq | 1.52 | | Sdq | 1.14 | | Sdq | 1.6 | |
| Sdr | 76.2 | % | Sdr | 68.4 | % | Sdr | 68.8 | % | Sdr | 44.9 | % | Sdr | 74.4 | % |
| ASME B46.1 3D Parameters | | | ASME B46.1 3D Parameters | | | ASME B46.1 3D Parameters | | | ASME B46.1 3D Parameters | | | ASME B46.1 3D Parameters | | |
| St | 74.5 | μm | St | 49.6 | μm | St | 59.6 | μm | St | 65.8 | μm | St | 49.1 | μm |
| SP 1.25 | 30% FP, 0.5mS JD | | Dentin 0.75 | 100% FP, 80uS PW | | Dentin 0.75 | 100% FP, 80uS PW | | Dentin 1.00 | 100% FP, 180uS PW | | Dentin 1.00 | 100% FP, 180uS PW | |
| Sample 6 etch | | | Sample 7 | | | Sample 7 etch | | | Sample 8 | | | Sample 8 etch | | |
| ISO 25178 | | | ISO 25178 | | | ISO 25178 | | | ISO 25178 | | | ISO 25178 | | |
| Height Parameters | | | Height Parameters | | | Height Parameters | | | Height Parameters | | | Height Parameters | | |
| Sq | 4.93 | μm | Sq | 24.8 | μm | Sq | 10.4 | μm | Sq | 50 | μm | Sq | 43 | μm |
| Ssk | 0.221 | | Ssk | 0.373 | | Ssk | 0.296 | | Ssk | -0.435 | | Ssk | 0.0881 | |
| Sku | 3.78 | | Sku | 3.09 | | Sku | 2.77 | | Sku | 3.01 | | Sku | 3.23 | |
| Sp | 23.5 | μm | Sp | 91.3 | μm | Sp | 58.3 | μm | Sp | 116 | μm | Sp | 151 | μm |
| Sv | 16.6 | μm | Sv | 63.2 | μm | Sv | 29.4 | μm | Sv | 164 | μm | Sv | 147 | μm |
| Sz | 40 | μm | Sz | 155 | μm | Sz | 87.7 | μm | Sz | 280 | μm | Sz | 299 | μm |
| Sa | 3.87 | μm | Sa | 19.5 | μm | Sa | 8.55 | μm | Sa | 40.5 | μm | Sa | 34.9 | μm |
| Hybrid Parameters | | | Hybrid Parameters | | | Hybrid Parameters | | | Hybrid Parameters | | | Hybrid Parameters | | |
| Sdq | 1.38 | | Sdq | 1.64 | | Sdq | 1.19 | | Sdq | 2.47 | | Sdq | 2.73 | |
| Sdr | 59 | % | Sdr | 76.8 | % | Sdr | 48.1 | % | Sdr | 131 | % | Sdr | 149 | % |
| ASME B46.1 3D Parameters | | | ASME B46.1 3D Parameters | | | ASME B46.1 3D Parameters | | | ASME B46.1 3D Parameters | | | ASME B46.1 3D Parameters | | |
| St | 40 | μm | St | 155 | μm | St | 87.7 | μm | St | 280 | μm | St | 299 | μm |

FIG. 14B

40uS ON-Time, 20 Pulses per Crater

| Crater OFF-Time Legend (µS) |||
|---|---|---|
| 500 | 1000 | 1500 |
| 2000 | 2500 | 3000 |
| 3500 | 4000 | 4500 |

SYSTEMS AND METHODS FOR PULSING AND DIRECTING A PULSED LASER BEAM TO TREAT DENTAL TISSUE

CROSS-REFERENCE TO RELATED APPLICATIONS

This application is a continuation of and claims the benefit of priority to U.S. patent application Ser. No. 15/587,525, titled "Systems and Methods for Pulsing and Directing a Pulsed Laser Beam to Treat Dental Tissue," filed May 5, 2017, which claims priority to U.S. Provisional Patent Application No. 62/332,586, titled "System and Methods for Pulsing and Directing a Pulsed Laser Beam to Treat Dental Tissue," filed May 6, 2016, the disclosures of both of which are incorporated herein by reference in their entireties.

TECHNICAL FIELD

This disclosure relates generally to laser based dental treatment techniques and, more particularly, to spatially and/or temporally described patterns for treating dental tissue by scanning a pulsed laser beam across a treatment region according to the patterns.

BACKGROUND

Lasers are known to be useful in a multitude of hard and soft tissue dental procedures, including: removing decay, cutting, drilling or shaping hard tissue, and removing or cutting soft tissue. A tooth has three layers. The outermost layer is the enamel which is the hardest and forms a protective layer for the rest of the tooth. The middle and bulk of the tooth is made up of the dentin, and the innermost layer is the pulp. The enamel and dentin are similar in composition and are roughly at least 70% mineral by weight, which is carbonated hydroxyapatite, while the pulp contains vessels and nerves. Lasers at a wavelength in a range of 9.3-9.6 micrometers are well absorbed by the hydroxyapatite that is a significant component of tooth and bone, making such lasers efficient in the removal of hard tissue. In general, the growth of $CO_2$ laser applications in dentistry has increased substantially, with the $CO_2$ laser wavelength bands ranging between 9.3 and 10.6 micrometers. Between 9.6 and 10.6 micrometers, phosphate absorption drops significantly and thus dental lasers optimized for the removal of hard tissue are generally operated in the 9.3-9.6 micrometer wavelength range.

Lasers have been found to be useful in the removal of dental material without the same need for local anesthetic that is required when a similar procedure is performed with a drill. Further, lasers do not make the noises and vibrations that are associated with dental drills. At least for these reasons, it has been the hope of many in the dental industry that lasers may replace the drill and remove or at least reduce much of the discomfort, anxiety, and fear from dental treatment.

SUMMARY OF THE INVENTION

Incorporation of laser beam scanning, through the use of a beam guidance system, allows the laser beam to be directed to different areas in the treatment zone in a controlled manner. Examples of a beam guidance system are described in U.S. Patent Application Pub. No. 2013-0059264A1, which is incorporated herein by reference. Laser beam scanning allows larger areas to be treated by the laser, than is possible with a single focused spot. A pattern can be used to define parameters associated with scanning, e.g., jump interval (time between one point and another in a laser pattern), dwell time (time spent at a single point in the pattern), geometry (locations of all of the points in a pattern), and point sequence. Parameters associated with the use of a pulsed laser with a beam guidance system are disclosed in detail in U.S. Patent Application Pub. No. 2014-0363784A1, which is incorporated herein by reference.

A pulsed laser system having no beam guidance system or scanning capabilities may pulse the laser through the use of only two parameters, pulse width and repetition rate. Previous studies performed at the University of California San Francisco and elsewhere have shown that dental hard tissue being treated by a 9.3 micron laser has a thermal relaxation time of around 2 µs. This value serves to help define the desirable limits for the pulse width parameter. However, little work has been done to define suitable ranges for parameters associated with beam guidance (e.g., scanning of the laser beam) during dental hard tissue treatment.

It can be advantageous for a dental laser to be used without anesthesia and to cut the tooth without forming recast, asperities, significant melting or carbonization. It has been discovered that parameters associated with beam guidance can accomplish these objectives. Furthermore, it may enable a dental laser device to be widely adopted, if the device is as simple for a dentist to use as a conventional drill. Therefore, there is a need for a dental laser system and method that automatically controls certain parameters associated with beam guidance and laser pulsing, in order to provide high quality clinical results with minimal intervention from the dentist.

In general, in one aspect, embodiments of the disclosure feature a method for removing a region of dental tissue. The method can include the step of directing a plurality of laser pulse bursts of a laser beam to respective tissue locations in a pattern within the region of dental tissue to form a plurality of abutting craters. The pattern can be a function of crater size, which is determined based at least in part on a width of the laser beam, energy per pulse of the laser beam, and a characteristic of the tissue. The abutting craters can include a pair of partially overlapping craters, a pair of tangent craters, and/or a pair of spaced craters separated up to a specified maximum distance.

In various embodiments, at least one laser pulse burst of the plurality of laser pulse bursts consists of a single laser pulse. In other embodiments, at least one laser pulse burst of the plurality of laser pulse bursts includes a plurality of laser pulses. In some cases, the pattern is a function of a desired smoothness of the plurality of abutting craters. For example, an amount of overlap between partially overlapping craters and/or the specified maximum distance can be a function of the desired smoothness of the plurality of abutting craters.

In some instances, the step of directing a plurality of laser pulse bursts can include directing a first laser pulse burst to a first tissue location to form a first crater and directing a next laser pulse burst to a second tissue location to form a second crater not abutting the first crater. In such instances, the step of directing a plurality of laser pulse bursts further includes directing additional laser pulse bursts to additional respective tissue locations to form additional respective craters, where no two consecutive laser pulse bursts are directed to tissue locations that form abutting craters. In some cases in which additional laser pulse bursts are directed to additional respective tissue locations to form additional respective craters, a distance between any pair of consecutive additional tissue locations is within ±25 percent of a distance between the first and the second tissue locations. Abutting craters can include (i) three partially overlapping craters, (ii) three tangent craters, and/or (iii) three spaced craters separated up to a specified maximum distance.

In some cases, the crater size is a function of a desired ablation efficiency (e.g., at least 50 percent of a theoretical maximum ablation efficiency). The ablation efficiency can be a function of a volume of the plurality of abutting craters and a total energy of the plurality of laser pulse bursts.

In general, in another aspect, embodiments of the disclosure feature a dental laser system for removing a region of dental tissue. The system can include a laser source for generating a plurality of laser pulse bursts of a laser beam; a beam guidance system adapted to direct the plurality of laser pulse bursts to respective tissue locations in a pattern within the region of dental tissue to form a plurality of abutting craters, where the abutting craters include (i) a pair of partially overlapping craters, (ii) a pair of tangent craters, and/or (iii) a pair of spaced craters separated up to a specified maximum distance; and a controller adapted to control the laser source and the beam guidance system such that the pattern is a function of crater size determined at least in part on a width of the laser beam, energy per pulse of the laser beam, and a characteristic of the tissue.

In various embodiments, at least one laser pulse burst of the plurality of laser pulse bursts consists of a single laser pulse. In other embodiments, at least one laser pulse burst of the plurality of laser pulse bursts includes a plurality of laser pulses. In some cases, the pattern is a function of a desired smoothness of the plurality of abutting craters. For example, an amount of overlap between partially overlapping craters and/or the specified maximum distance can be a function of the desired smoothness of the plurality of abutting craters.

In some instances, the beam guidance system is further adapted to direct a first laser pulse burst to a first tissue location to form a first crater and direct a next laser pulse burst to a second tissue location to form a second crater not abutting the first crater. In such instances, the beam guidance system can be further adapted to direct additional laser pulse bursts to additional respective tissue locations to form additional respective craters, where no two consecutive laser pulse bursts are directed to tissue locations that form abutting craters. In some cases in which the beam guidance system is adapted to direct additional laser pulse bursts to additional respective tissue locations to form additional respective craters, a distance between any pair of consecutive additional tissue locations is within ±25 percent of a distance between the first and the second tissue locations. Abutting craters can include (i) three partially overlapping craters, (ii) three tangent craters, and/or (iii) three spaced craters separated up to a specified maximum distance.

In some cases, the crater size is a function of a desired ablation efficiency (e.g., at least 50 percent of a theoretical maximum ablation efficiency). The ablation efficiency can be a function of a volume of the plurality of abutting craters and a total energy of the plurality of laser pulse bursts. In some cases, the beam guidance system includes a galvanometer.

In general, in another aspect, embodiments of the disclosure feature another method for removing a region of dental tissue. The method can include the steps of directing a first laser pulse burst to a first tissue location in a pattern of tissue locations within the region of dental tissue, directing at least one additional laser pulse burst to at least one additional non-adjacent tissue location in the pattern, and directing a next laser pulse burst to a tissue location in the pattern adjacent to the first tissue location, where a quantity of additional non-adjacent tissue locations is determined based, at least in part, on (i) a thermal relaxation time corresponding to melting of the dental tissue and (ii) a property of the laser pulses.

In various embodiments, the property of the first laser pulse burst is a laser pulse period, an ON duration of a laser pulse, a burst frequency, and/or a burst ON duration. The quantity of additional non-adjacent tissue locations can be up to 10 (or more), e.g., one. In some cases, the first laser pulse burst and/or the next laser pulse burst consists of a single laser pulse. In other cases, the first laser pulse burst and/or the next laser pulse burst includes a plurality of laser pulses. The total time of the at least one additional laser pulse burst can be approximately equal to the thermal relaxation time.

In general, in another aspect, embodiments of the disclosure feature another dental laser system for removing a region of dental tissue. The system can include a laser source for generating a plurality of laser pulse bursts of a laser beam; a beam guidance system adapted to (i) direct a first laser pulse burst to a first tissue location in a pattern of tissue locations within the region of dental tissue, (ii) direct at least one additional laser pulse burst to at least one additional non-adjacent tissue location in the pattern, and (iii) direct a next laser pulse burst to a tissue location in the pattern adjacent to the first tissue location, where a quantity of additional non-adjacent tissue locations is determined based, at least in part, on a thermal relaxation time corresponding to melting of the dental tissue and a property of the laser pulses.

In various embodiments, the property of the first laser pulse burst is a laser pulse period, an ON duration of a laser pulse, a burst frequency, and/or a burst ON duration. The quantity of additional non-adjacent tissue locations can be up to 10 (or more), e.g., one. In some cases, the first laser pulse burst and/or the next laser pulse burst consists of a single laser pulse. In other cases, the first laser pulse burst and/or the next laser pulse burst includes a plurality of laser pulses. The total time of the at least one additional laser pulse burst can be approximately equal to the thermal relaxation time. In some cases, the beam guidance system includes a galvanometer.

BRIEF DESCRIPTION OF THE DRAWINGS

Various aspects this disclosure will become more apparent in view of the attached drawings and accompanying detailed description. In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 5A-5B show an example geometry and example laser operating parameters for a 1.25 mm pattern, according to various embodiments;

FIGS. 6A-6B show an example geometry and example laser operating parameters for a 1.00 mm pattern, according to various embodiments;

FIGS. 7A-7B show an example geometry and example laser operating parameters for a 0.75 mm pattern, according to various embodiments;

FIGS. 8A-8B show an example geometry and example laser operating parameters for a 0.50 mm pattern, according to various embodiments;

FIGS. 9A-9B show an example geometry and example laser operating parameters for a 0.25 mm pattern, according to various embodiments;

FIG. 11 is a chart showing example data for pulse width and energy per pulse for an example dental laser system, according to various embodiments;

FIG. 12 shows confocal microscope images of dental enamel treated with various patterns, according to various embodiments;

FIG. 13 is a table showing example laser operating parameters and variables related to single pulse patterns, according to various embodiments;

FIGS. 14A-14B are tables listing example surface roughness data for surfaces treated with various patterns, according to various embodiments;

DETAILED DESCRIPTION

In various embodiments, this disclosure relates to a laser based dental treatment system that delivers laser pulses in unique and advantageous patterns. Laser pulses may be used to remove or ablate tissue, e.g., dental tissue. When the laser beam has a wavelength that is well coupled into the material being ablated (e.g., approx. 3.0, 9.3 or 9.6 microns for enamel and dentine), as well as sufficient pulse fluence (e.g., greater than 2 $J/cm^2$ for a 9.3 micron beam), a single pulse of the laser beam can successfully ablate some material. Single pulse ablation generally forms a crater in the material being treated. Typically, in order to ablate fully a selected tissue region, several craters must be formed.

Figure 1:
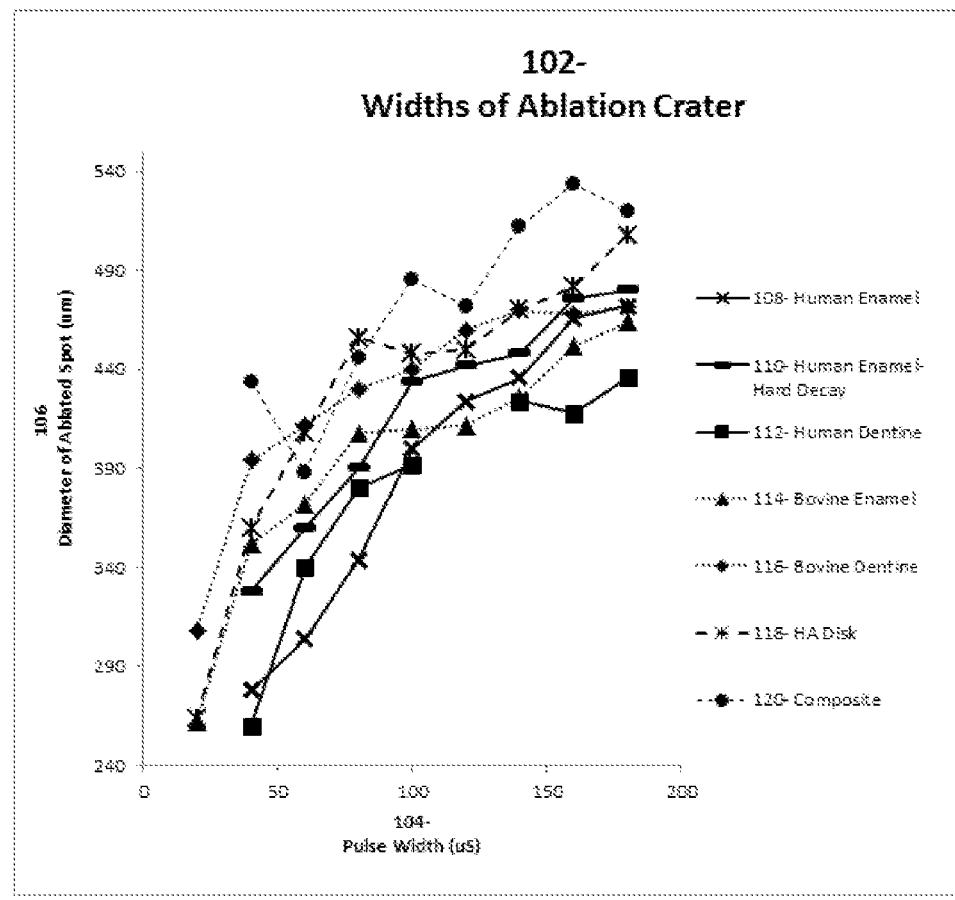
FIG. 1 is a graph showing example data for the diameter of an ablated spot as a function of pulse width, for various materials.

FIG. 1 is a graph, 102, that depicts an example relationship between pulse width (microseconds), 104, and diameter of a crater (micron), 106, resulting from ablation caused by a single pulse for various materials, when using a 9.3 micron wavelength laser beam. Materials graphed include: human enamel, 108, hard decay in human enamel, 110, human dentine, 112, bovine enamel, 114, bovine dentine, 116, hydroxyapatite disk, 118, and dental composite, 120. An example of an isotopic carbon dioxide laser source capable of generating a 9.3 micron wavelength beam at suitable power levels is a Coherent E-150i laser (Coherent Inc., Santa Clara, Calif.). During the single pulse ablation, a mist flow was used at a nominal volumetric flow rate of 15 ml/min. This rate was chosen, as it is about the maximum mist flow rate of some commercial embodiments of the Solea® dental laser system (Convergent Dental, Natick, Ma.). Mist can attenuate the laser energy reaching the treatment region and, at least in some instances, mist has an effect on the size of the craters formed by a single pulse. Crater size is defined in more detail below. It can be seen from FIG. 1 that in some cases the diameter of the ablation crater, 106, generally increases with pulse width, 104, and that typically softer materials yield larger crater diameters for the same pulse width. As used here, pulse width and pulse duration indicate the ON time of a pulse and not the total pulse period, which includes both the pulse ON time and pulse OFF time of a single pulse, which may repeat at a frequency that is the reciprocal of the pulse period.

Figure 2A:
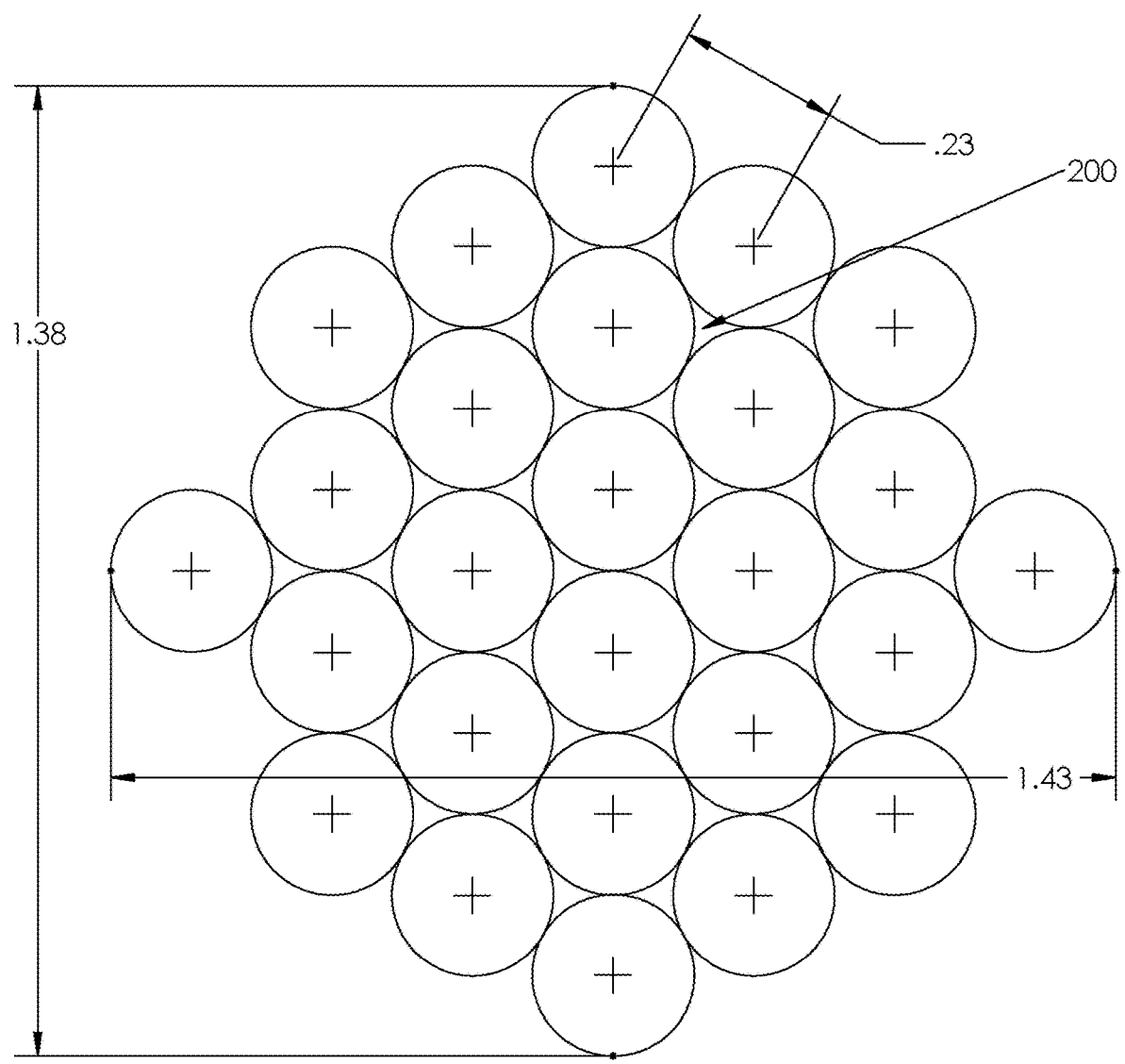
FIGS. 2A-2E show example ablation patterns, according to various embodiments.

A pattern, as the term is used herein, defines certain spatial and/or temporal parameters associated with scanning or moving a pulsed laser beam in a region of tissue to be ablated. FIG. 2A shows an example ablation pattern with 0.231 mm pattern spacing, having an overall pattern width of about 1.43 mm and an overall height or length of about 1.38 mm. Pattern spacing generally means the spacing between adjacent locations to which the laser beam is targeted so that craters would be formed around those locations. The spacing between adjacent craters, called resulting crater spacing, would depend on the diameters of the craters, as discussed below.

Figure 2B:
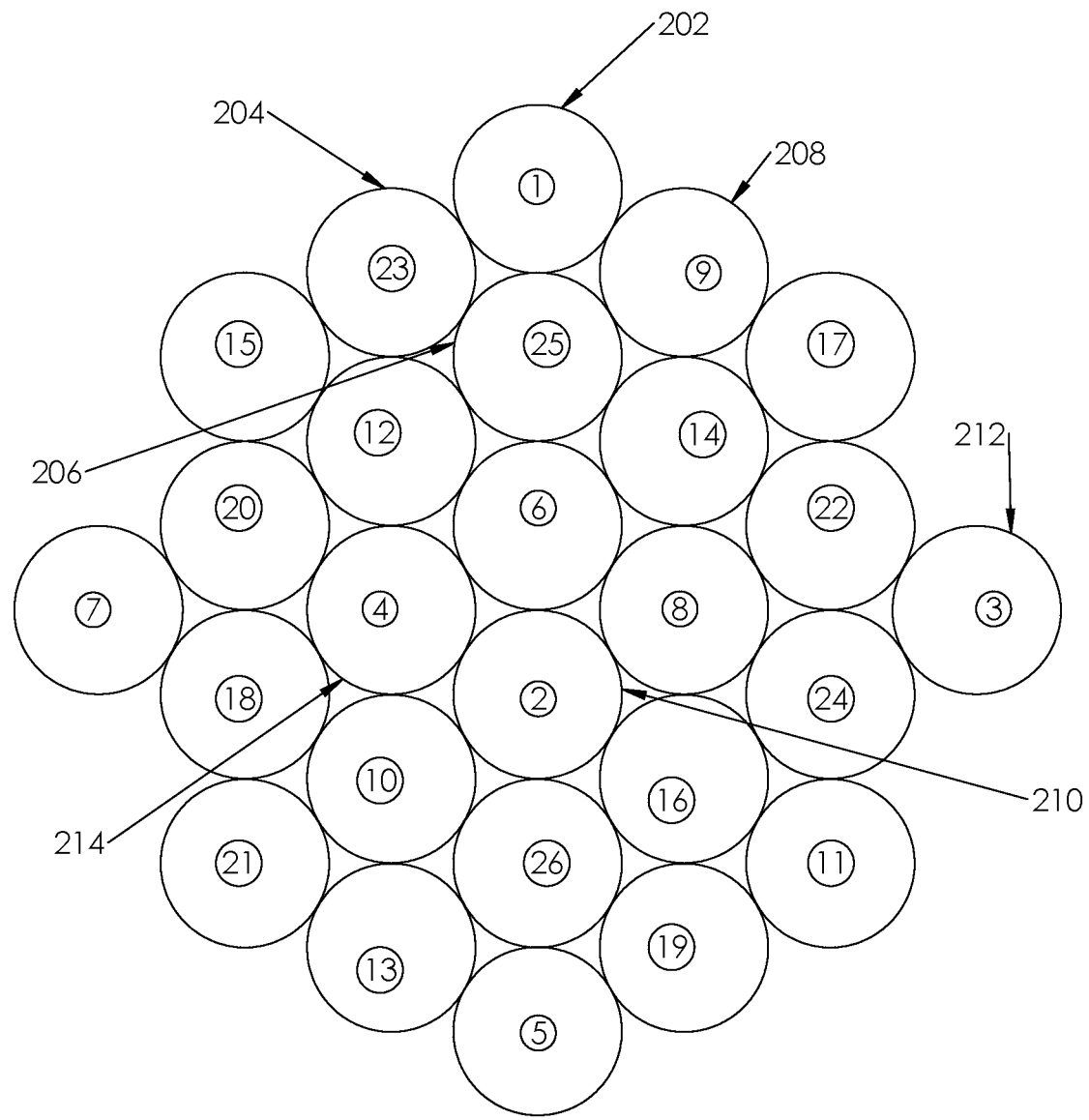

In this example illustration, the center of each circle represents a location at which a laser pulse (or burst of laser pulses) is directed to create an ablation crater around the center (represented by the crosshair). The circle itself represents the full cross-sectional area of the ablated crater, where the diameter of the crater is approximately (e.g., within a tolerance of ±1%, ±5%, ±10%, ±20%, etc.) equal to the pattern spacing (0.231 mm). As shown, the ablation pattern includes circles arranged in a packed or tightly nested form. FIG. 2B shows the same example pattern as FIG. 2A and labels the order in which the 26 craters are scanned, which can be repeated (in some cases, with an offset position). By varying the spacing between the sequentially targeted locations in the pattern, it was discovered that different materials can be ablated more or less efficiently.

In various embodiments, the laser beam is scanned in a pattern by a beam guidance system, which may feature at least one galvanometer. Laser pulsing and control of the beam guidance system may be achieved through a controller, such as a laser marking controller. An example of a suitable scan controller is the LEC-1 Ethernet-based embedded scan controller (Lanmark Controls Inc., Acton, Ma.).

Figure 2C:
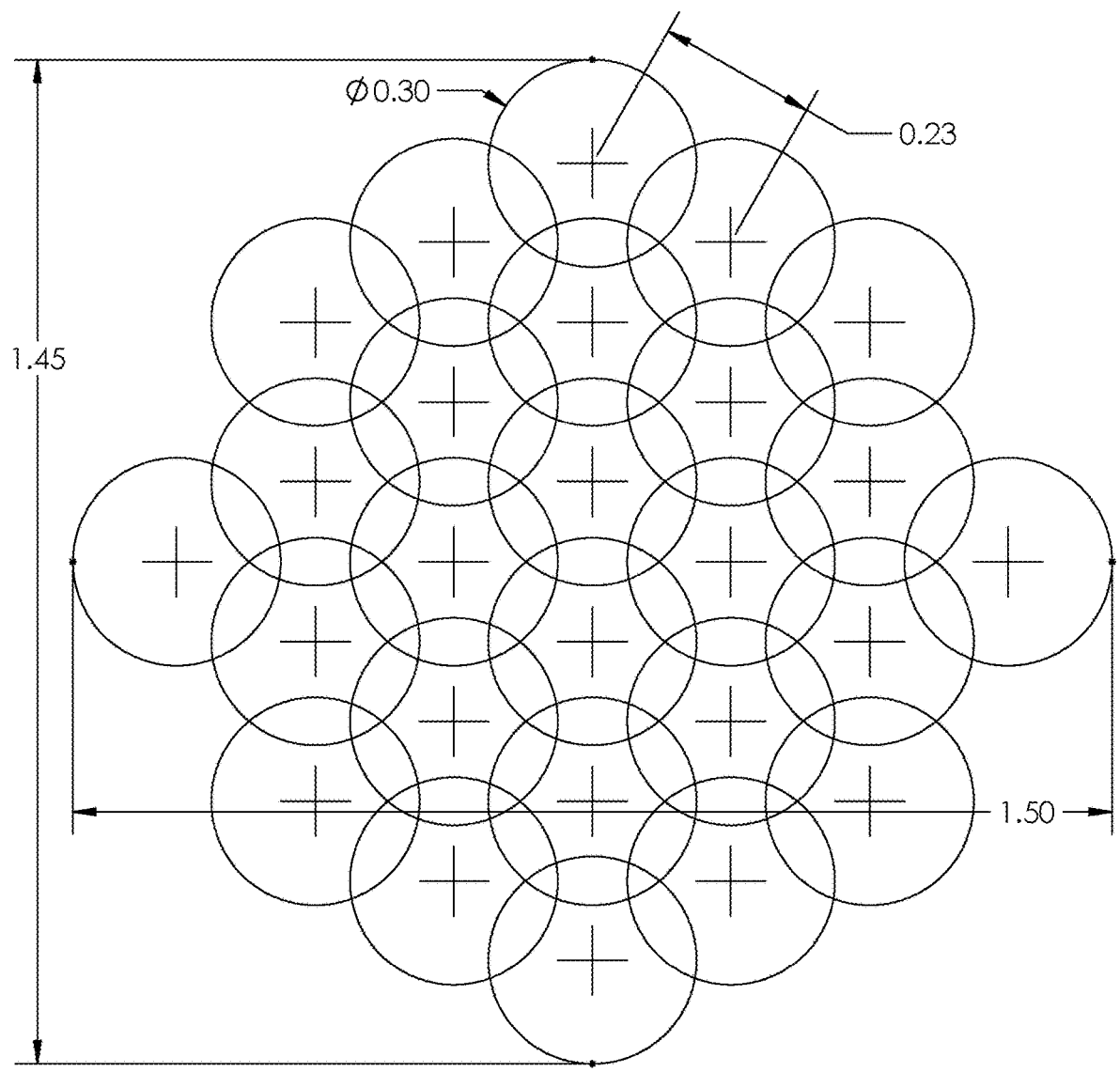
Figure 2D:
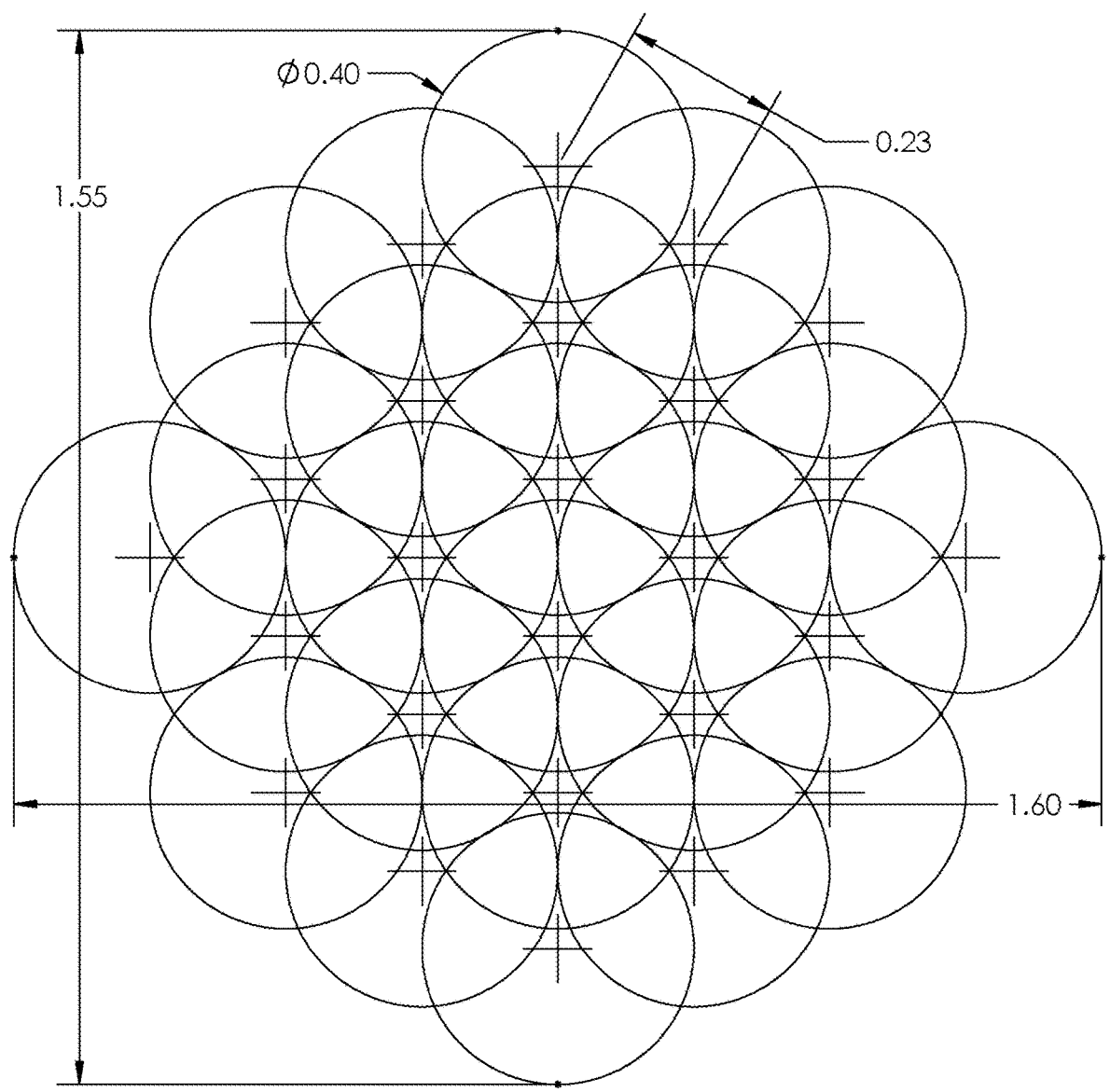
Figure 2E:
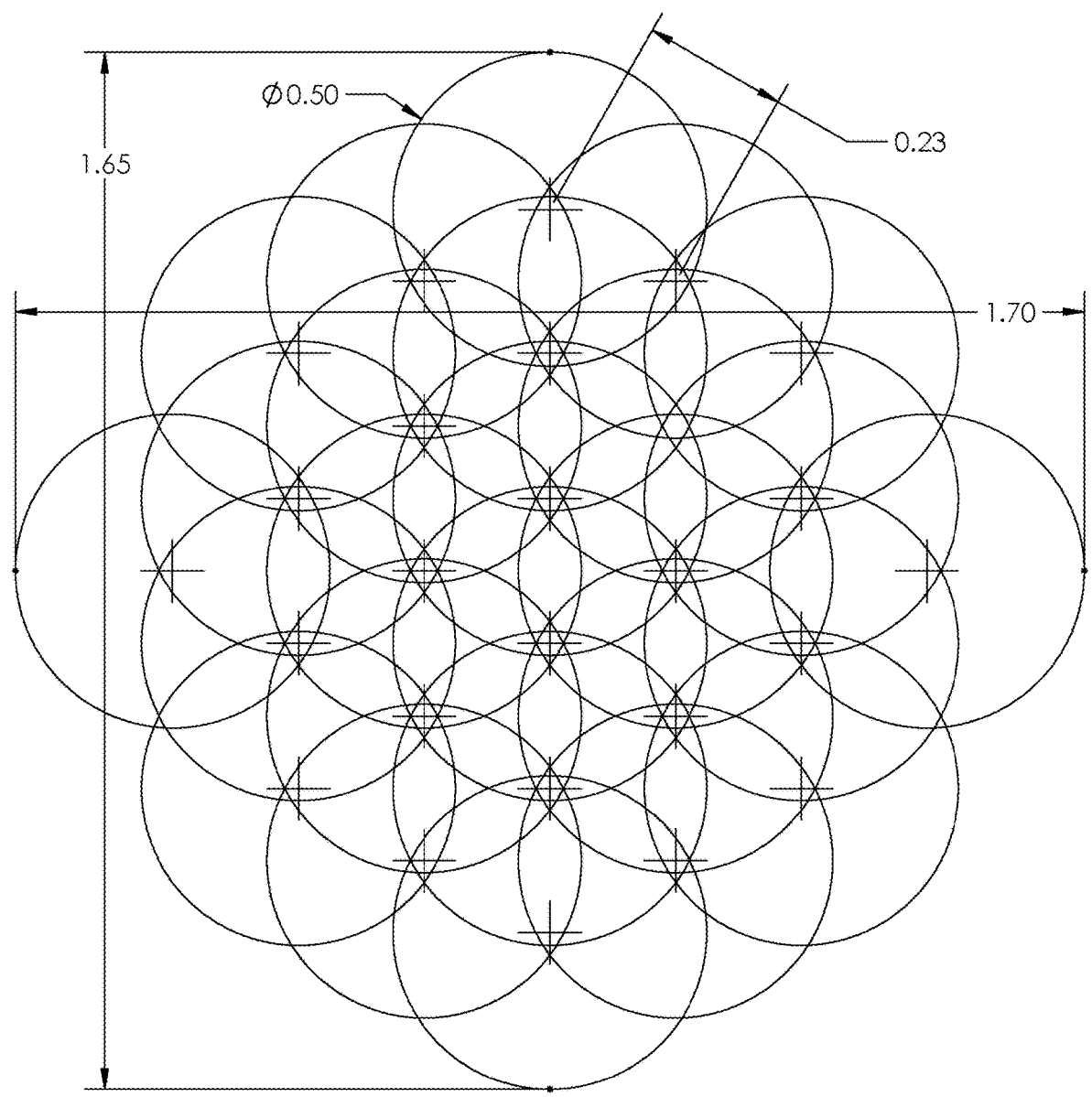

FIGS. 2C-2E illustrate the example ablation pattern from FIG. 2A, with each FIG. 2C-2E illustrating the example resulting crater patterns having craters of a different size. As used in the context of FIGS. 2A-2E, the same pattern spacing means the same spacing is chosen between the locations to which the laser beam is targeted to form craters around those locations; the crater size, however, can be different and, as such, the resulting crater spacing can be different. The resulting crater spacing can be described as the minimum distance between two closest craters after all the craters are formed according to a selected pattern. In FIG. 2A, the formed craters are tangential and, as such, the resulting crater spacing is approximately 0 mm (with a tolerance of, e.g., ±1%, ±2%, ±5%, ±20%, etc.). As FIG. 2A shows, even though the resulting crater spacing is approximately 0 mm, there are gaps, i.e., untreated regions, such as the gap 200, in the overall treatment region.

FIG. 2C shows the example pattern where a pulse burst results in a crater having a 0.3 mm diameter and a pattern with overall width of about 1.5 mm and length of about 1.45 mm. In general, a pulse burst includes several (e.g., 10, 20, 50, 200, etc.) pulses, but a pulse burst can include only a single pulse. FIG. 2D shows the example pattern, where a pulse burst results in a crater having a 0.4 mm diameter and a pattern with overall width of about 1.6 mm and length of about 1.55 mm. FIG. 2E shows the example pattern, where a pulse burst results in a crater having a 0.5 mm diameter and a pattern with overall width of about 1.7 mm and length of about 1.65 mm. As indicated in the dimensions in the figures, larger craters cause the effective size of the pattern, i.e., the total size of the region that is ablated, to increase, depending on pattern spacing, resulting crater spacing, and overlap. The craters shown in FIGS. 2C-2E overlap. As such, the resulting crater spacing in these examples is negative. The minimum distance between two closest craters after all the craters are formed according to a selected pattern, i.e., the resulting crater spacing, can be a number greater than zero, however. In this case, the two closest craters are neither overlapping nor tangential.

As used herein, the size of a crater refers to a surface area or a cross-sectional width (e.g., a diameter) of the crater at the treatment surface, and not the depth or the volume of the crater though, in some cases, size (i.e., the surface area and/or the diameter) and volume are related. For example, the craters in FIG. 2E having a 0.5 mm diameter have a greater size than the craters in FIG. 2D having a 0.4 mm diameter, which have a greater size than the craters in FIG. 2C having a 0.3 mm diameter (note that surface area is a function of diameter). In general, the craters are not perfectly circular. Therefore, a crater diameter can be the diameter of a circle approximating the crater, where the cross-sectional area of the circle is plus or minus 0.1%, 0.5%, 1%, 2%, 5% 10%, 20%, etc., of the cross-sectional area of the crater at the tissue surface. In such instances, crater size is still a measure of the crater's surface area at the treatment surface. The crater size typically depends on a number of factors (e.g., one or more laser parameters such as pulse width, pulse period, a number of pulses in a burst directed to a single spot, energy per pulse, burst frequency, pulse profile, spot size, etc., and/or one or more properties of the material to be treated). In various embodiments of a dental treatment system described herein, the pattern spacing and sequentially targeted point/location spacing (discussed below) can be preselected and/or controlled, e.g., by adjusting the galvo-controller mirror step. The crater diameter can be controlled by adjusting one or more laser parameters, e.g., beam width. The parameter resulting crater spacing can be controlled by selecting a suitable pattern spacing and laser parameters (which would control the crater diameter). As discussed below, the smoothness of a treated surface may generally depend on the resulting crater spacing.

In order to quantify the volumetric material removal rate of different ablation patterns, an ablation rate gauge and procedure was used. The rate gauge allows an operator to place a material (e.g., human molar, bovine enamel, composite block, etc.) into a fixture, attach a dental laser system, and then ablate the material at a set amount of time and power, while holding various other laser parameters (e.g., pulse width, pulse period, number of pulses in a burst, etc.) constant. Ablation of dental hard tissues with pulsed dental lasers typically require the use of a cooling mist. The ablation rate gauge also allows the operator to use mist at a set coolant flow rate for the experiments.

In various experiments, the volumetric amount of material removed by an ablation pattern (e.g., shown in FIGS. 2A-2E), was observed to depend on the spacing between the centers of the craters, when all other variables and parameters of treatment (including laser power, pulse width, etc.) are held constant. As used herein, the spacing between crater centers is a distance between two adjacent spots to each of which one or more laser pulses are directed so as to form respective craters around those spots. This distance is sometimes referred to herein as crater spacing or pattern spacing.

Figure 3A:
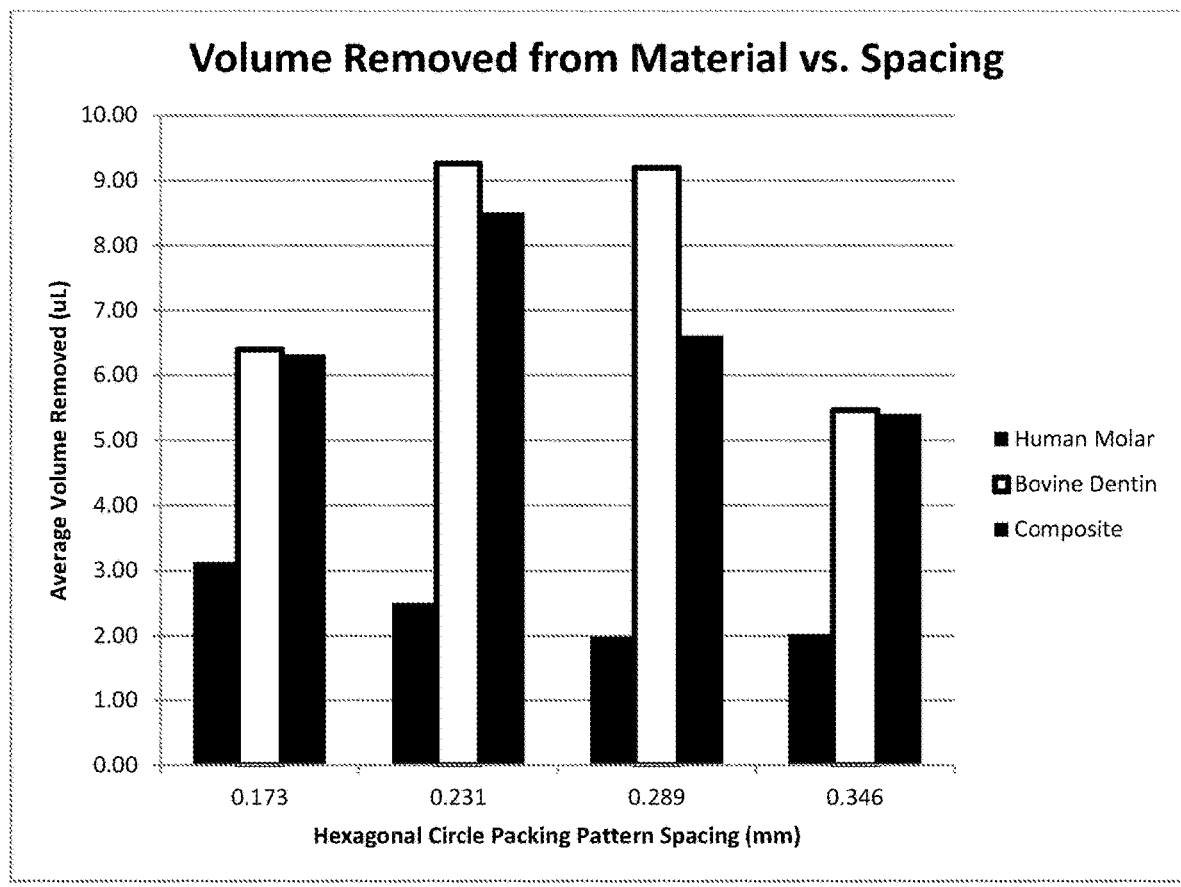
FIG. 3A is a chart showing example data for average volume removed as a function of pattern spacing, for various materials.

FIG. 3A provides example data for the average volume removed as a function of the pattern spacing, for various materials. It can be observed from FIG. 3A that for Bovine dentin and composite materials, the volumetric removal rate peaks when the crater spacing is 0.231 mm, and the rate decreases when the spacing is decreased (e.g., to 0.173 mm) or increased (e.g., to 0.346 mm). For human molar, the volumetric removal rate is maximum when the crater spacing is 0.173 mm and the rate monotonically decreases as the spacing is increased.

In general, during the treatment of dental tissue the outermost hard enamel layer may need to be ablated before the inner relatively softer dentin layer, which may be infected and/or decayed, can be removed. Depending on the depth at which the decayed, softer dentine is located and/or the volume of such dentine needing to be removed, the ablation process may unavoidably remove some surrounding healthy hard enamel. If the crater size (e.g., diameter) is small, it may be possible to minimize the ablation of healthy hard enamel, but the volumetric rate of removal of the decayed softer tissue may be low, requiring a longer treatment time. On the other hand, forming large craters can result in rapid removal of the decayed tissue, but the removed volume of the surrounding healthy, hard tissue may also increase.

Figure 3B:
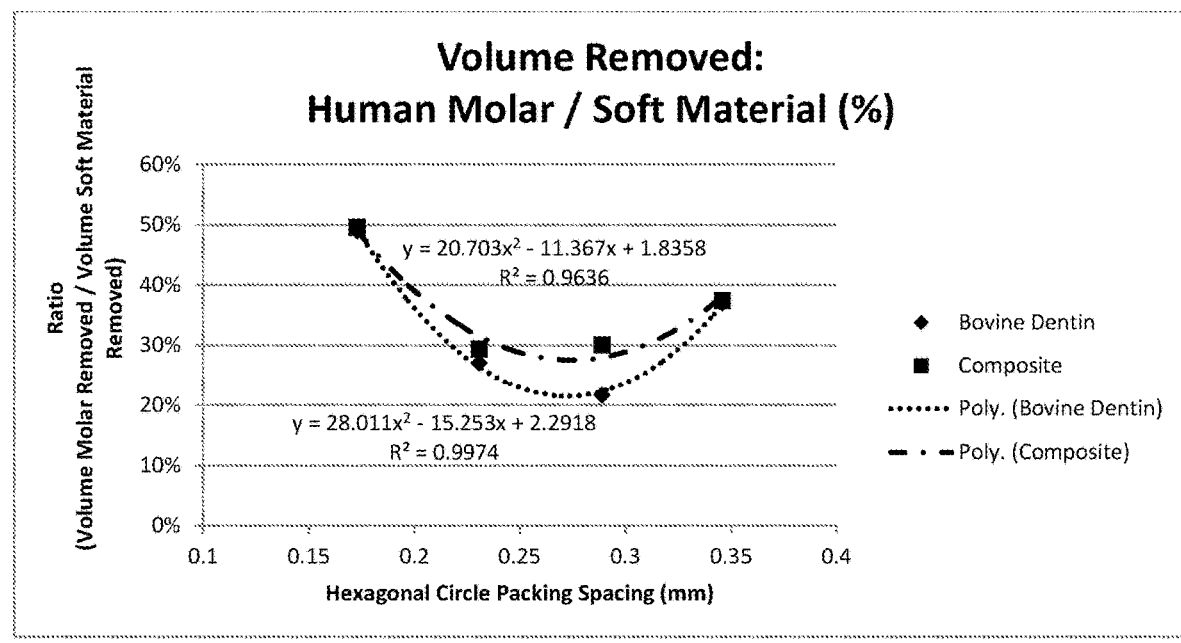
FIG. 3B is a graph showing example data for the ratio of hard material removed to soft material removed as a function of pattern spacing, for various materials.

In various embodiments, it is desirable to maximize the volume of the soft or decayed tissue that is ablated and removed while minimizing the volume of the healthy, hard tissue that is also ablated and removed. As such, an experiment was performed to identify an optimized crater spacing that maximizes relative removal of softer materials and provides the greatest difference in volumetric material removal rate for softer materials and volumetric material removal rate for harder materials. FIG. 3B plots example data for the ratio of the volume of harder material (e.g., enamel) removed to the volume of softer material (e.g., composite or bovine dentine) removed as a function of crater spacing, for two softer materials, namely, bovine dentine and composite material.

The data for each material shows that the ratio is minimized when the crater spacing is about 0.28 mm. At this spacing, in this experiment, the volumetric removal rate for softer decayed tissue (e.g., composite) is at least three times as great as the volumetric removal rate for harder tissue (e.g., healthy enamel). This experiment shows that when various laser beam parameters such as energy per pulse, pulse width, pulse period, number of pulses in a burst directed to a spot, number of bursts directed to a spot, etc., are selected, the pattern spacing can be adjusted such that diseased tissue is removed much more quickly than healthy tissue, for minimally invasive dental preparations.

Figure 3C:
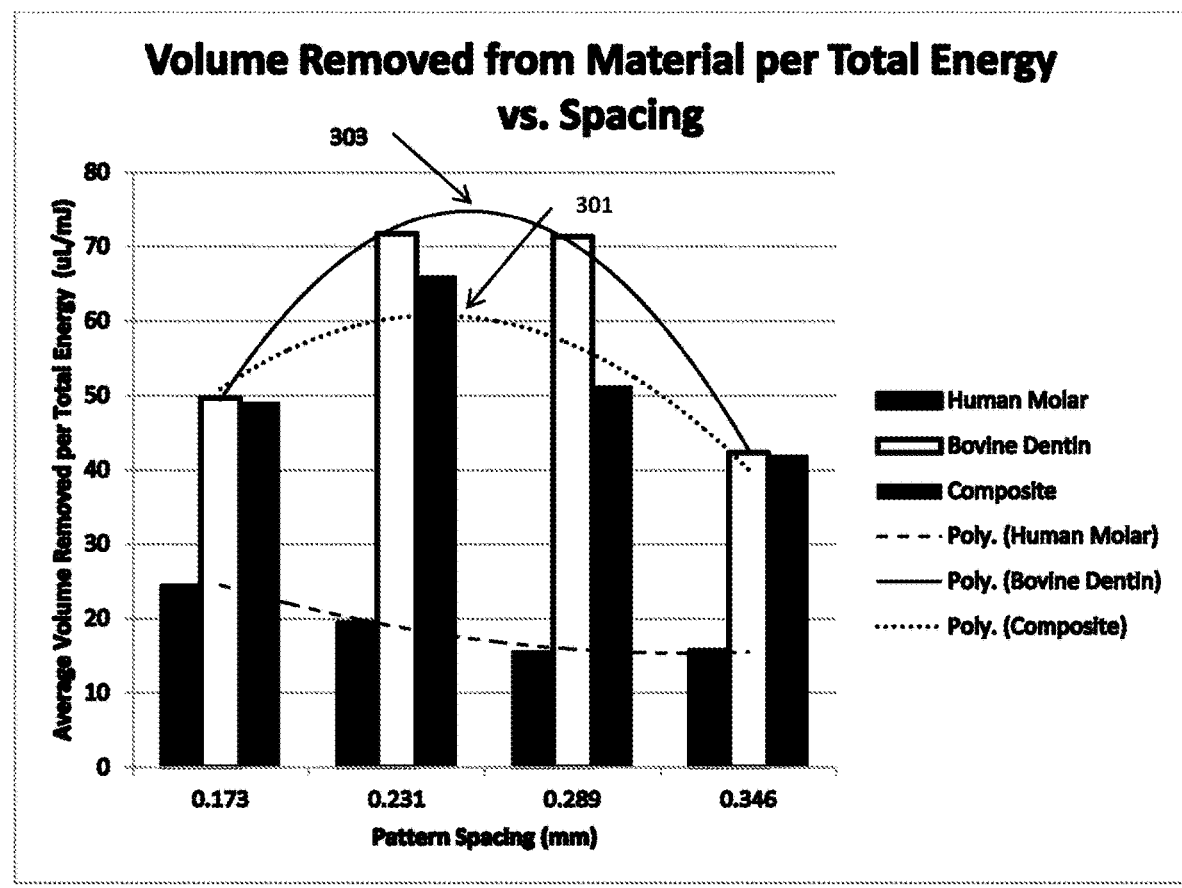
FIG. 3C is a chart showing example data for average volume removed per total energy as a function of pattern spacing, for various materials.

In various embodiments, the crater size and/or spacing can be based upon a desired ablation efficiency, as opposed to a differential ablation rate in various materials (as described above). An experiment was conducted to demonstrate this capability. Referring to FIG. 3C, example data for the average volume removed per total energy delivered per burst as a function of crater spacing is provided, for various materials. For the composite and bovine dentin materials, a maximum ablation efficiency, curves 301 and 303, respectively, is shown. The maximum ablation efficiencies coincide with the local maximum of the best fit polynomial equations that fit the observed data. It should be noted that in the spacing range shown in FIG. 3C, there is no local maximum for human molar material. This is because the maximum ablation efficiency for human molar occurs at a spacing narrower than 0.173 mm center-to-center distance (which is the narrowest spacing shown in FIG. 3C).

Figures 4A, 4B:
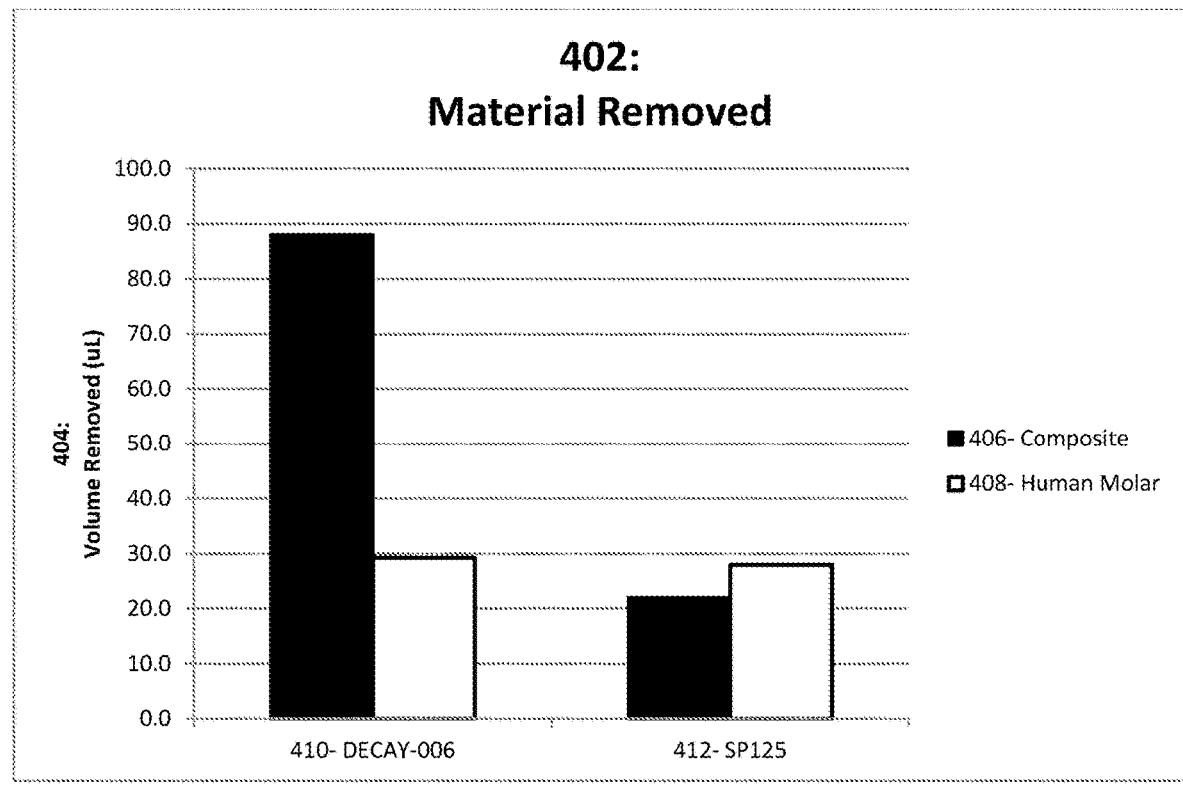
FIG. 4A is a chart showing example data for volumetric removal performance for an example pattern developed for cutting decayed tissue and an example pattern developed for cutting healthy dental tissue.
FIG. 4B shows example operating parameters for a laser used to deliver the patterns described in the chart shown in FIG. 4A.

In some embodiments, one or more parameters of the laser beam is adjusted to maximize the volumetric removal rate, in addition to or as an alternative to adjusting the crater spacing. FIG. 4A, for example, is a graph, 402, showing volume of material removed along a vertical axis (microliters), 404. The graph, 402, shows volume removed for composite, 406, and human molar, 408, after being modified by two different ablation patterns operating for 233 Seconds at a constant 11.2 W average laser power. A first ablation pattern, 410, (labelled DECAY-006) has a geometry and location sequence described in FIGS. 2A-2B. The first ablation pattern, 410, is developed to cut softer materials, such as decay and composite at a faster rate than hard materials, such as healthy enamel. The volume removed, 404, from a second ablation pattern, 412, (labelled SP125) is shown in comparison to the volume removed, 404, to the first ablation pattern, 410. The second ablation pattern (SP125), 412, is developed for cutting healthy dental hard tissue, and has a geometry and location sequence described below in reference to FIG. 5A.

The results depicted in FIG. 4A were obtained by operating each ablation pattern 9 times, in a 3×3 grid, on each material. The total amount of energy delivered by each ablation pattern was held constant, as both cut time and average power were constant for each ablation pattern. The cut time being 233 Seconds; and, the average power being 11.2 W. In order to achieve constant cut time and average power, different laser and beam guidance parameters were used for DECAY-006 and SP125. These parameters are summarized in FIG. 4B. Referring to FIG. 4B, DECAY-006 required a laser pulse duration of 60 microseconds, a beam guidance jump speed delay of 1 mS, and 589 passes. SP125 required a laser pulse duration of 32.5 microseconds, a beam guidance jump delay of 0.5 mS, and 652 passes.

In various embodiments, the crater size and/or spacing can be based upon a desired smoothness of an ablated region. As used herein, ablated region refers to the remaining portion of a tissue surface after the tissue has been ablated by the laser. Defined another way, the ablated region is the void created by all of the craters formed during delivery of the laser pulses. As one example, the ablated region can be the void created when a decayed portion of a tooth is removed (e.g., into which a filling material may be inserted). A comparison of FIGS. 2B and 2C illustrates how a relationship between crater size and pattern spacing can affect the smoothness of the ablation region. Specifically, though the pattern spacing, i.e., the spacing between the locations targeted to form craters, is the same (as in FIGS. 2A-2E), the laser parameter(s) can be selected such that the crater sizes are different. As such, the spacing between craters after the formation thereof, i.e., resulting crater spacing, can be different. In FIG. 2A, the resulting crater spacing is such that small gaps are left between the ablation craters (an example gap, 200, is labelled in FIG. 2A). These gaps represent material that is not removed, at least in some cases. Conversely, in FIG. 2C the resulting crater spacing is different, such that the gaps generally do not exist. Thus, all else being equal, the same ablation pattern produces one resulting crater spacing shown in FIG. 2A and another resulting crater spacing shown in FIG. 2C. The resulting crater spacing shown in FIG. 2A leaves behind more material than the resulting crater spacing shown in FIG. 2C and, therefore, the ablation craters formed as shown in FIG. 2A is less even, less flat, and less smooth than the ablation craters shown in FIG. 2C.

In general, if the craters do not overlap, and are tangential or if the respective crater boundaries when closest to one another are spaced apart, there is little or no repeated ablation in a region that has already been ablated once. This can minimize the speed of treatment. The larger the resulting crater spacing, however, the larger the area of the gaps between such non-overlapping craters. This can leave a number of areas untreated within the overall region to be treated, resulting in a treated region having a more rough surface. Such surface roughness can be reduced by decreasing the crater size and/or reducing pattern spacing (e.g., to maintain tangential craters), which can increase the number of craters within the region to be treated and, as such, the total treatment time. If adjacent craters are treated sequentially, the exchange of heat induced in the tissue while ablating the next adjacent spot can cause unwanted charring and/or melting of enamel in the previously ablated spot.

One way to ensure that the entire region to be treated is actually ablated is to form overlapping craters. Here again, some portions of the tissue may be treated several, e.g., three or more, times while some tissue portions may be treated only once or twice. Thus, overlapping craters can also result in a rough tissue surface after treatment. In addition, if overlapping craters are formed by directing laser pulses to adjacent spots in succession, the exchange of heat induced in the tissue while ablating one spot to the adjacent spot can cause unwanted charring and/or melting of enamel. In general, one or more treatment characteristics can be optimized by selecting a suitable pattern spacing, crater size, crater spacing, and/or a sequence in which selected spots are ablated, forming craters around those spots. The treatment characteristics can include smoothness of the treated surface, charring or melting of enamel, overall treatment time, patient sensation, treatment efficiency in terms of volumetric removal rate as a function of total energy delivered to the treatment region, etc.

Figure 5A:
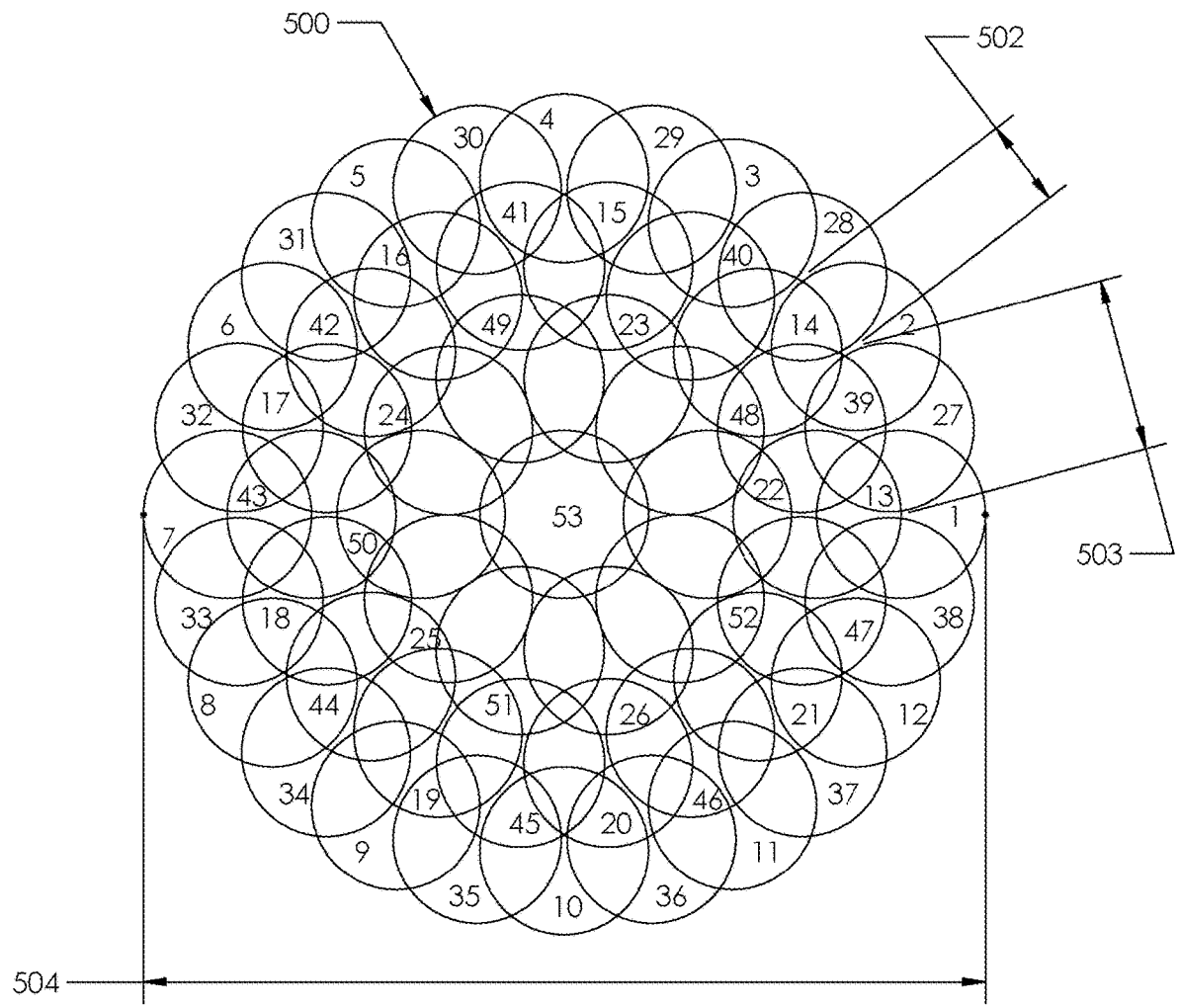

Various other patterns having a corresponding pattern spacing selected to accomplish a particular performance objective are contemplated. For example, FIGS. 5A-5B define one pattern developed for cutting dental hard tissue, referred to herein as the SP125 pattern. FIG. 5A depicts the sequence in which 53 craters are created as the laser is scanned by the beam guidance system. Various pulse parameters are selected such that the nominal size of the craters, 500, formed (described in terms of the crater diameter) is 0.25 mm within a tolerance of ±20%. The nominal pattern spacing between adjacent target points, 502, for the SP125 pattern is 0.13 mm within a tolerance of ±20%. The nominal spacing between sequentially targeted points (i.e., the distance between two consecutively selected target locations), 503, for the SP125 pattern is 0.25 mm within a tolerance of ±20%. As FIG. 5A shows, the adjacent target points/locations are not necessarily targeted sequentially. To illustrate, crater 27 overlaps with (and is closest to) crater 1. After the location around which crater 1 is formed, however, the immediately next location to which the laser beam is directed is not the center of crater 27; instead, it is the center of crater 2. Crater 27 is formed later, after forming various other craters at other locations. In this example, the nominal diameter, 504, of the treatment region that is covered by the pattern is 1.25 mm within a tolerance of ±20%. FIG. 5B includes Tables 1-3 that provide the laser operating parameters for the SP125 pattern.

Figure 6A:
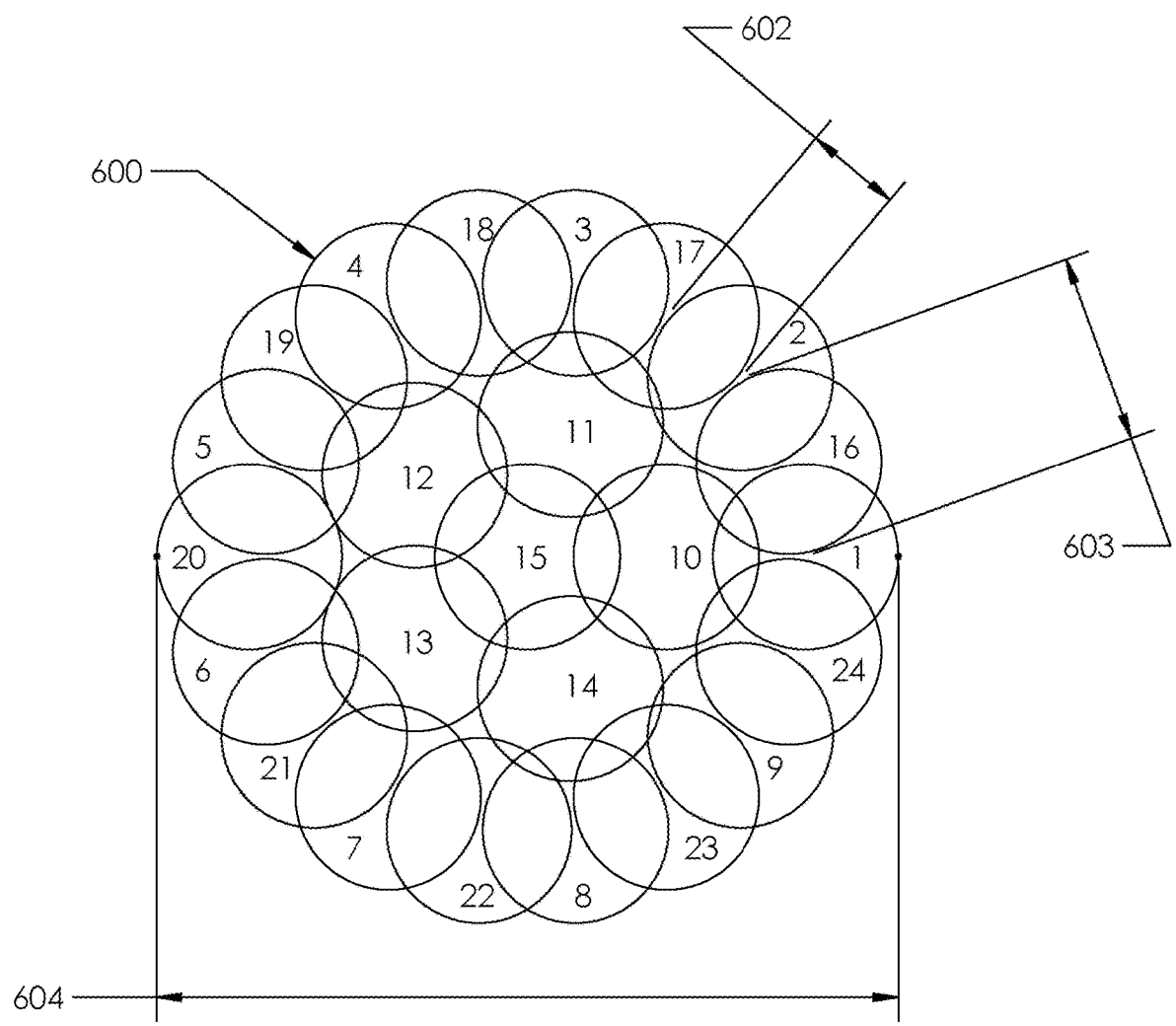

FIGS. 6A-6B define another pattern developed for cutting dental hard tissue, referred to herein as the SP100 pattern. FIG. 6A depicts the sequence in which the 24 craters are created as the laser is scanned by the beam guidance system. Here again, various pulse parameters are selected such that the nominal size of the craters, 600, formed (described in terms of the crater diameter) is 0.25 mm within a tolerance of ±20%. The nominal pattern spacing between adjacent target points, 602, for the SP100 pattern is 0.13 mm within a tolerance of ±20%. For some sequentially targeted points, 603, the nominal spacing is 0.25 mm within a tolerance of ±20%. The nominal diameter, 604, of the treatment region that is covered by the pattern is 1.00 mm. FIG. 6B includes Tables 1-3 that provide the laser operating parameters for the SP100 pattern.

Figure 7A:
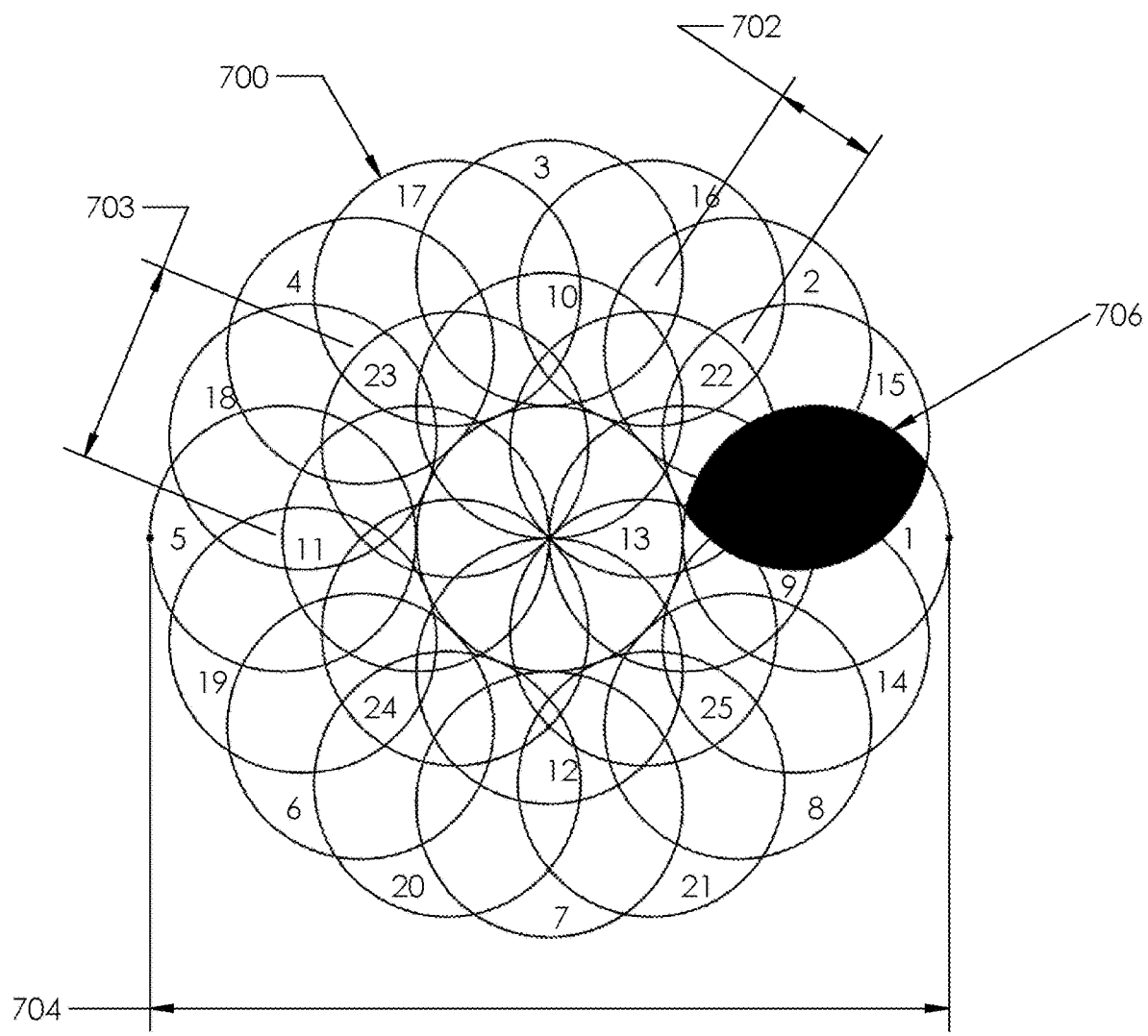

FIGS. 7A-7B define another pattern developed for cutting dental hard tissue, referred to herein as the SP075 pattern. FIG. 7A depicts the sequence in which the 25 craters are created as the laser is scanned by the beam guidance system. Various pulse parameters are selected such that the nominal size, 700, of the craters formed (described in terms of the crater diameter) is 0.25 mm within a tolerance of ±20%. The nominal pattern spacing between adjacent target points, 702, for the SP075 pattern is 0.10 mm within a tolerance of ±20%. The nominal spacing between sequentially targeted points, 703, for the SP075 pattern is 0.19 mm within a tolerance of ±20%. And, the nominal diameter, 704, of the treatment region that is covered by the pattern is 0.75 mm within a tolerance of ±20%. As shown in FIG. 7A, the SP075 pattern includes intersection areas defined by the intersection of two or more craters. One example intersection area, 706, is labelled in FIG. 7A. FIG. 7B includes Tables 1-3 that provide the laser operating parameters for the SP075 pattern.

Figure 8A:
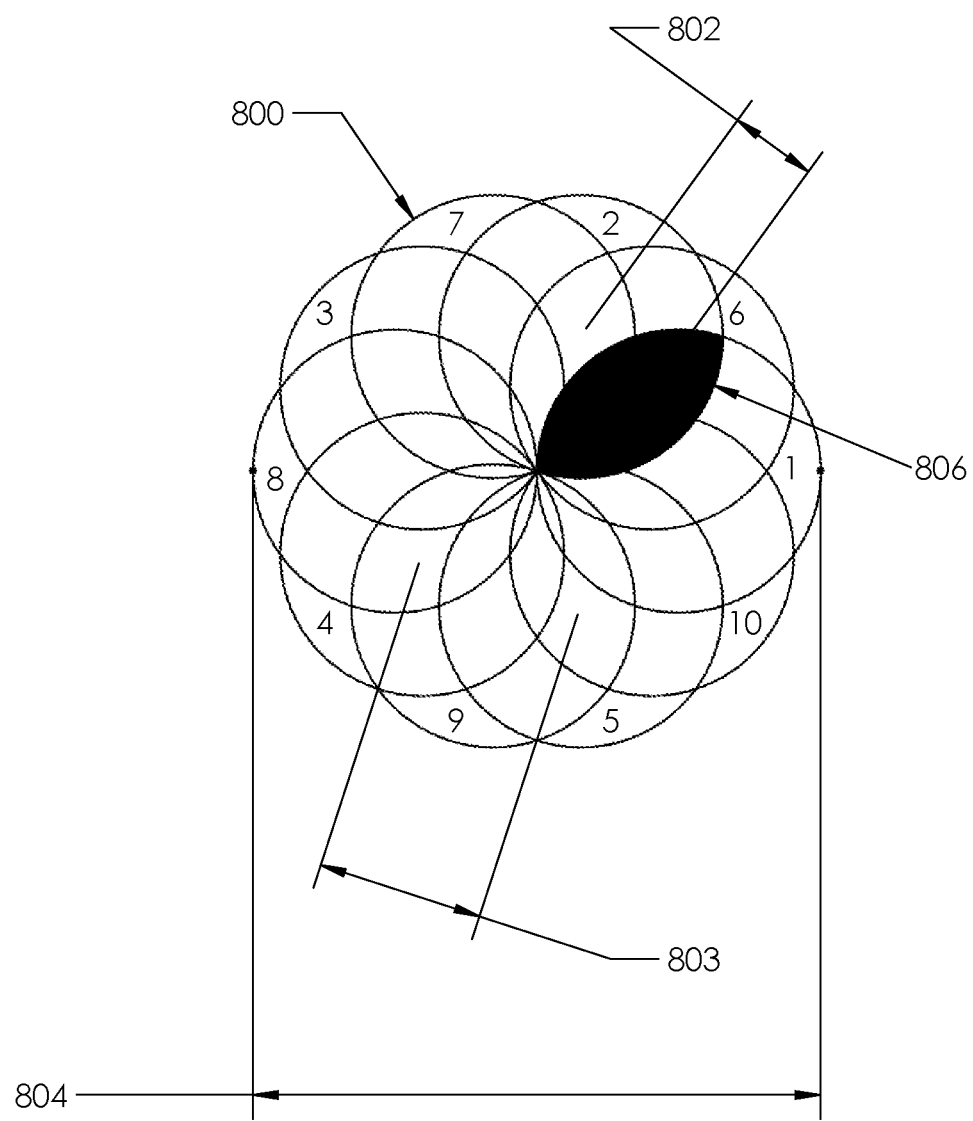

FIGS. 8A-8B define another pattern developed for cutting dental hard tissue, referred to herein as the SP050 pattern. FIG. 8A depicts the sequence in which the 10 craters are created as the laser is scanned by the beam guidance system. Various pulse parameters are selected such that the nominal size, 800, of the craters formed (described in terms of the crater diameter) is 0.25 mm within a tolerance of ±20%. The nominal pattern spacing between adjacent target points, 802, for the SP050 pattern is 0.08 mm within a tolerance of ±20%. The nominal spacing between sequentially targeted points, 803, for the SP050 pattern is 0.15 mm within a tolerance of ±20%. And, the nominal diameter, 804, of the treatment region that is covered by the pattern is 0.50 mm within a tolerance of ±20%. As shown in FIG. 8A, the SP050 pattern includes intersection areas defined by the intersection of two laser pulse locations. One example intersection area, 806, is labelled in FIG. 8A. The typical spacing between adjacent target points for the SP050 pattern is shorter than for the SP075 pattern but the nominal crater size in both patterns is about the same (0.25 mm), resulting in larger intersection areas in the SP050 pattern. FIG. 8B includes Tables 1-3 that provide the laser operating parameters for the SP050 pattern.

Figure 9A:
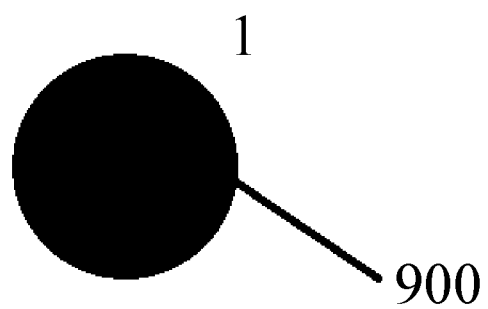

FIGS. 9A-9B define another pattern developed for cutting dental hard tissue, referred to herein as the SP025 pattern. FIG. 9A depicts the sequence in which the craters are created as the laser is scanned by the beam guidance system. Various pulse parameters are selected such that the nominal size of the craters formed (described in terms of the crater diameter), 900, is 0.25 mm within a tolerance of ±20%. The nominal pattern spacing between adjacent target points for the SP025 is 0 mm within a tolerance of ±20%, i.e., effectively there is only one point location in the pattern. The nominal diameter of the pattern is 0.25 mm within a tolerance of ±20%. As there is only one pulse location in the SP025 pattern, the entire area of the pulse location is considered an intersection area, 900. FIG. 9B includes Tables 1-3 that provide the laser operating parameters for the SP025 pattern.

While FIGS. 5A, 6A, 7A, 8A, and 9A depict a generally circular treatment region covered by the respective patterns, it should be understood that this is illustrative only and that in general the treatment region covered by a pattern can have any regular shape (e.g., square, rectangle, oval, hexagon, etc.) or may have a user defined irregular shape bounded by straight-line segments and/or curves.

Returning to FIG. 1, the crater size is shown to be a function of pulse width in some cases. FIGS. 5A, 6A, 7A, 8A, and 9A show craters that are circular and 0.25 mm in diameter within a tolerance of ±20%. As indicated above, this is a nominal crater size (diameter) used for demonstration only. In practice, the size (diameter) of the crater can be varied according to a number of laser parameters, for example: pulse width, energy per pulse, number of pulses in a burst directed to a location, quantity of mist flow, and material being ablated. Further, for a given pattern, generally defined, at least in part, by the selected pattern spacing, the intersection areas can increase with increased crater size. Generally, longer pulse widths, softer materials, and/or greater pulse energies contribute to larger intersection area sizes, given a particular ablation pattern geometry and crater spacing.

In various embodiments, the timing of the creation of ablation craters can also contribute to the performance of ablation, either independently of or in addition to the spacing between the craters. Specifically, in some instances, a pattern can be defined, at least in part, by a minimum amount of time that should elapse between the end of one pulse burst (which may include one or more pulses) at one location and the start of another pulse burst at an adjacent location, where the craters formed at the two locations are abutting. As used herein, abutting locations refer to locations at which the craters formed overlap each other, are tangential to each other, or the closest points on the crater boundaries are spaced apart by a specified maximum distance. In general, directing laser energy to a location has a thermal effect on an adjacent location, especially if the craters formed at the two adjacent locations are abutting craters. Specifically, the heat induced in the tissue at one location can flow to affect the tissue at the adjacent location.

When ablating enamel, if the amount of time between the end of one laser pulse burst (having one or more laser pulses) and the start of another laser pulse burst directed to the same or an adjacent location is less than a threshold minimum amount of time, the other laser pulse burst can cause recast (the re-forming of ablated material about the treatment region), moderate to severe melting of the unablated tissue, and/or asperities. When ablating dentin, such negative effects can include charring or carbonization of the dentin. These negative effects, in some instances, are the result of unintended heat accumulation in the unablated tissue.

Previous attempts to achieve clinically viable parameters for a dental laser system incorporating a beam guidance system are described in U.S. Patent Application Pub. No. 2014-0363784A1, which is incorporated herein by reference. These previous attempts describe the use of a burst of multiple laser pulses at a single location, followed by a long delay (e.g., >1 ms) and a second burst of multiple pulses at the same or a second, adjacent location. Typically these bursts are executed at high rates, e.g., greater than 1 kHz, and in some cases greater than 5 kHz. This burst mode allowed for lower energies per pulse, e.g., about 10 mJ with pulse widths of about 40 μs, to achieve ablation at clinically viable rates.

Figure 10:
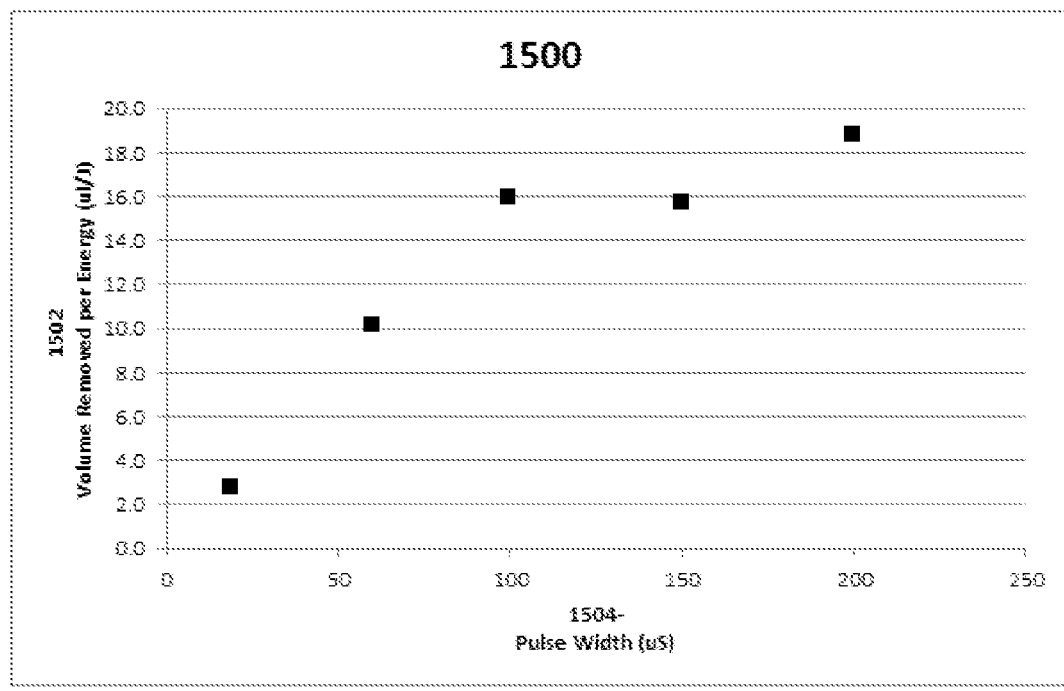
FIG. 10 is a graph showing example data for volume removed per unit energy as a function of pulse width, for human enamel.

FIG. 10 is a graph, 1000, that shows example data for the efficiency of material removal of human enamel as a function of pulse width. The data shown in FIG. 10 was collected by holding constant the average power, ablation time, and mist flow of a laser system having a wavelength of 9.3 micron and a peak power between of about 400 W. The graph, 1000, has a vertical axis, 1002, representing volume removed per energy (microliters per Joule) and a horizontal axis, 1004, representing pulse width (microseconds). FIG. 10 shows that material is removed more efficiently (i.e., more mass removed per laser energy), for longer pulse widths. Pulse energy is typically related to pulse width in a near linear relationship, so it can be appreciated from FIG. 10 that greater pulse energies generally produce greater material removal efficiency. FIG. 11 shows example data indicating the relationship between pulse width and pulse energy for a laser system comparable to that used in FIG. 10. In general, peripheral heating occurs at longer pulse widths, where the pulse width is significantly longer, e.g., ten or twenty times longer, than the thermal relaxation time of the target material. The thermal relaxation time for a 9.3 μm laser pulse in enamel is about 2 μs. Therefore, longer pulse widths (e.g., about 100 μs), while more efficient at material removal, can also heat the unablated tissue more than shorter pulse widths (e.g., between 5-50 μs), where the pulse width is up to 10 times, up to 20 times, up to 50 times, etc. the thermal relaxation time of the material to be ablated.

In various embodiments, the laser energy is delivered such that the pulse width is long enough to ablate tissue with a single laser pulse, which can result in efficient cutting. However, in order to avoid melting or other negative effects, the amount of time between successive pulses at a particular location or at adjacent locations may be increased beyond that used in the burst pulse technique described in U.S. Patent Application Pub. No. 2014-0363784A1. For example, the SP1.25 pattern is a pattern having a long enough pulse width to ablate tissue with a single laser pulse ("SP" is shorthand for single pulse, and all SP patterns referred to herein have this characteristic). The minimum amount of time between ablations for any given intersection area for the SP1.25 pattern is about 0.8 mS. The minimum amount of time between successive ablations of the same location in successive ablation layers in a layer-by-layer ablation, using a single pulse for each point for the SP1.25 pattern is equal to the amount of time it takes to repeat the pattern, which for SP1.25 is about 52 ms. It should be understood that these times are illustrative only and that these times, in general, may depending on one or more of the selected pattern spacing, crater diameter, resulting crater spacing, spacing between sequentially targeted points/locations, and one or more laser-pulse parameters. These times are much longer than the amount of time between individual pulses of a burst used in a laser burst pattern. A table showing example timing variables related to the various SP patterns is shown in FIG. 13.

FIG. 12 shows confocal microscope images taken of preparation walls of an enamel sample after ablation with four different laser patterns. The patterns are referred to herein with the following labels: 1.25 XC, 1202, 1.25 M, 1204, Dentin 1.00, 1206, and SP1.00, 1208. Three of these laser patterns (1.25 XC, 1202, 1.25 M, 1204, and Dentin 1.00, 1206) are created with a burst pulse method and hit a single intersection area or a single pulse location with multiple laser pulses in quick succession (e.g., less than 0.4 ms and typically less than 0.2 mS). The fourth pattern, SP1.00, 1208, is created with a single pulse per location method. The preparation wall for SP 1.00, 1208, is more uniform, even and flat than the other three, 1202, 1204, and 1206. A straight preparation wall is conventionally desirable for restorations, as it allows for a better seal between the restoration and the dental tissue.

As described above, crater spacing can have an effect on the smoothness of the ablation region. Specifically, overlapping craters or abutting craters having a small size (diameter) can increase the smoothness of the treated surface. Forming abutting craters (i.e., overlapping, tangential, or closely spaced craters) in succession, however, can cause unwanted side effects, such as melting of the enamel or charring of dentine. This can be avoided as described below by selecting a sequence for forming a crater pattern where abutting craters are generally not formed in succession.

Figure 15A:
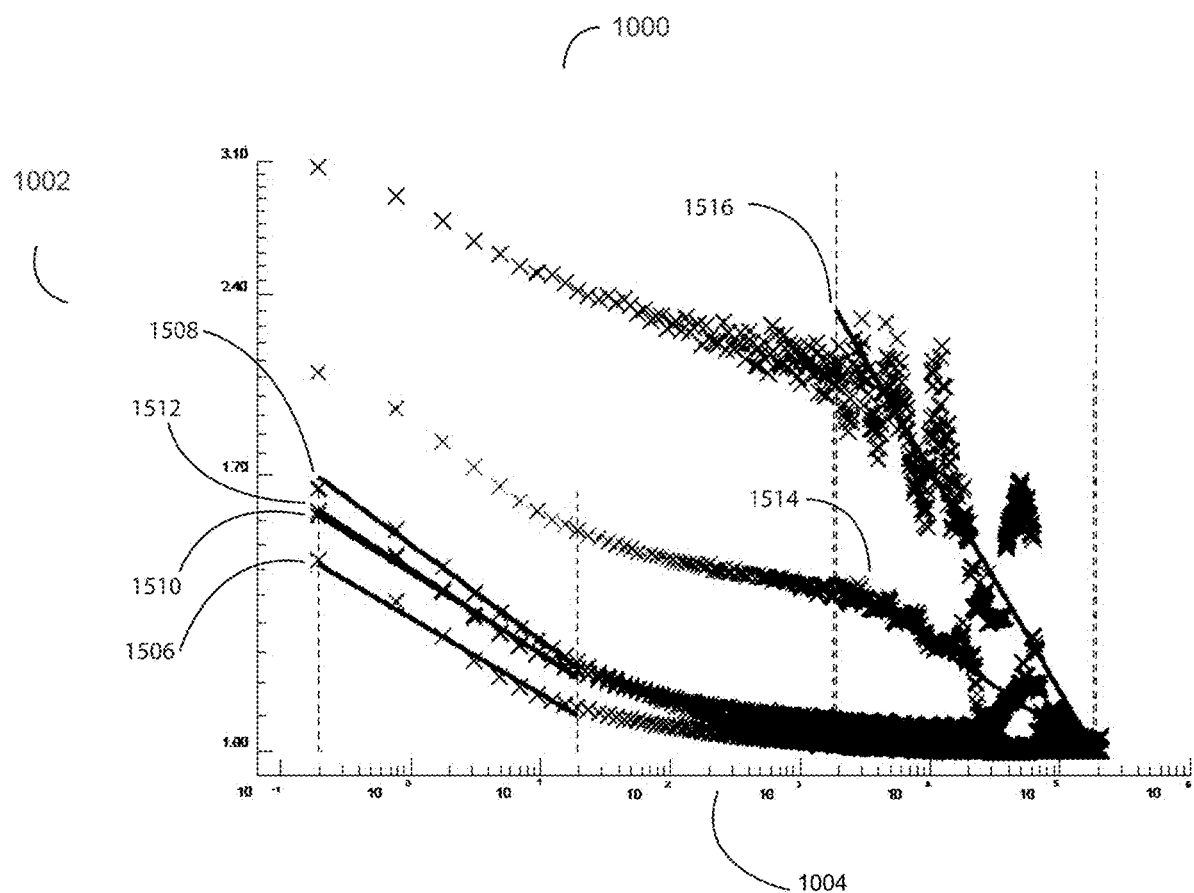
FIGS. 15A-15B are plots showing example fractal scale surface roughness data for surfaces treated with various patterns, according to various embodiments.

FIGS. 14A-14B quantify the smoothness of ablation regions cut with different patterns, by providing example data for the surface roughness in an ablation region cut with three single pulse patterns (SP0.75, SP1.00, and SP1.25) and three burst pulse patterns (XC0.75, XC1.00, and XC1.25). In particular, FIGS. 14A-B are tables showing data measurements of the dimensions of surface features within the ablation regions cut by each of these patterns. As shown, the height parameters for each of the single pulse patterns are smaller than the height parameters for the corresponding burst pulse patterns, which indicates that single pulse patterns provide a smoother ablation region than burst pulse patterns. FIG. 14A shows the measured surface features on bovine enamel and FIG. 14B shows the measured surface features on bovine dentin. Fractal scale analysis plots of the samples from FIGS. 14A-14B are provided in FIG. 15A and FIG. 15B, respectively. Fractal scale analysis is described in U.S. Pat. No. 5,307,292, and incorporated herein by reference. Briefly, in fractal scale surface analysis a measured surface is tessellated with triangles of common area, and a ratio of a sum total of all the triangle's areas divided by a projected area of the measured surface is found. The ratio is calculated for numerous triangle sizes, or scales. Referring to FIGS. 15A, a graph, 1500, illustrating the surface roughness in bovine enamel has a vertical axis, 1502, representing the ratio (no units) and a horizontal axis, 1504, representing the scale (microns squared). In general, the higher the ratio, the rougher the measured surface is. The graph, 1500, shows analysis of bovine enamel surfaces resulting from preparations using a number of different patterns. The different patterns are the same as is documented in FIG. 14A, and include single pulse per location patterns: SP 0.75, 1506, SP 1.00,1508, and SP 1.25, 1510; as well as, patterns having multiple pulses per location: XC 0.75, 1512, XC 1.00, 1514, and XC 1.25, 1516. It should be appreciated that the single pulse patterns produce a lower ratio in bovine enamel at all scales when compared to the multiple pulses per location patterns.

Figure 15B:
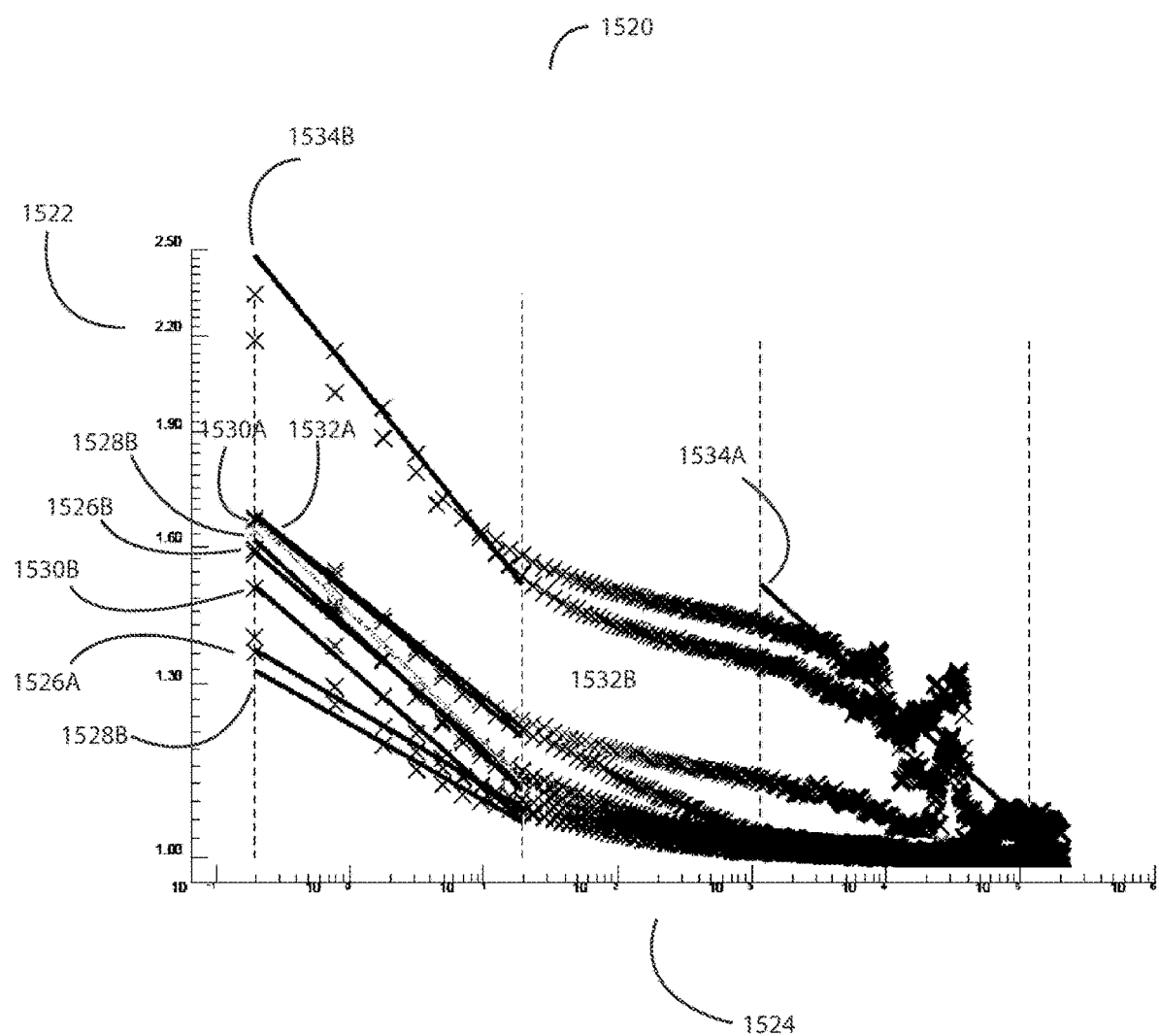

Referring now to FIG. 15B, a graph 1520, illustrating surface roughness in bovine dentin has a vertical axis, 1522, representing the ratio (no untis) and a horizontal axis, 1524, representing the scale (microns squared). The graph, 1520, shows analysis of bovine dentin surfaces resulting from preparations using a number of different patterns. The different patterns are the same as is documented in FIG. 14B, and include single pulse per location patterns: SP 0.75, 1526A, SP 0.75 with acid etch, 1526B, SP 1.00, 1528A, SP 1.00 with acid etch, 1528B, SP 1.25, 1530A, and SP 1.25 with acid etch, 1530B; as well as, patterns having multiple pulses per location: Dentin 0.75, 1532A, Dentin 0.75 with acid etch, 1532B, Dentin 1.00, 1534A, and Dentin 1.00 with acid etch, 1534B. It should be appreciated that the single pulse patterns produce a lower ratio in bovine dentin at all scales when compared to the multiple pulses per location patterns.

Figure 16:
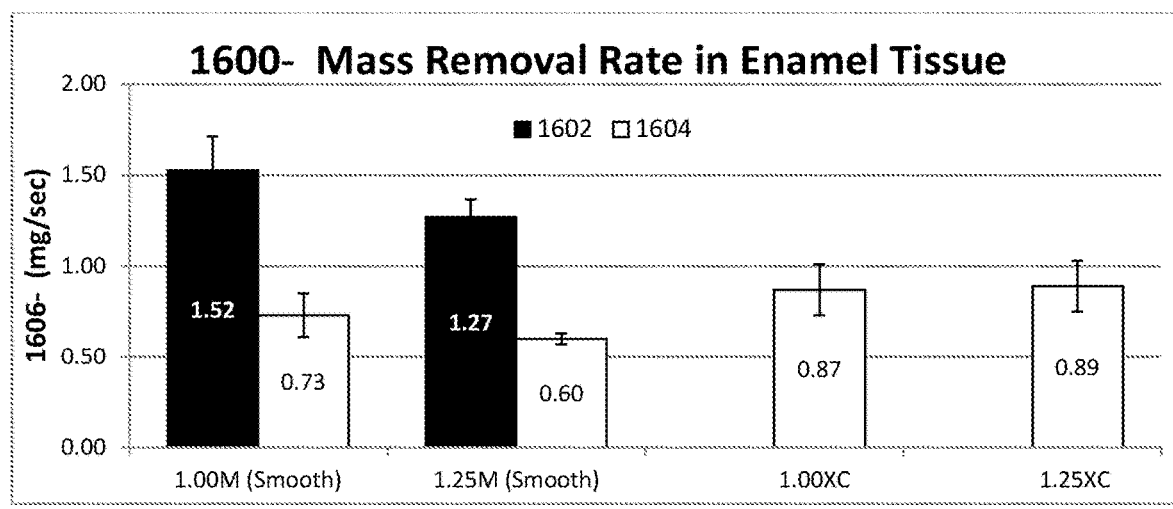
FIG. 16 is a graph showing example data for mass material removal rate of enamel tissue for various patterns, according to various embodiments.

Additionally, in various embodiments, the single pulse patterns achieve a faster material removal rate than burst pulse patterns. For example, FIG. 16 is a graph, 1600, that shows example data for mass removal rate, for various patterns, including patterns having a single pulse per location, 1602, and patterns having multiple pulses (a single burst) per location, 1604. The graph, 1600, has a vertical axis, 1606, that represents mass removal rate (milligrams per second). This data was generated by collecting time and weight measurements while each pattern cut an enamel tooth sample having dimensions of approximately 2×2×4 mm. In FIG. 16, the 1.00M (SMOOTH), 1.25M (SMOOTH), 1.00XC, and 1.25XC labels refer to different pattern spacings/geometries. The 1.25M (SMOOTH) pattern/geometry was used to cut a region to be treated in one instance using a burst of pulses, where each burst applied 12 pulses per location and, in another instance, using a single pulse per location. Similarly, the 1.00M (SMOOTH) pattern/geometry was used to cut a region to be treated in one instance using a burst of pulses where each burst applied 6 pulses per location and, in another instance, using a single pulse per location. The results, as shown in FIG. 16, indicate that for each pattern the single pulse ablation achieved a material removal rate of greater than two times the rate achieved using the same pattern using multiple pulse burst-mode ablation. During ablation of enamel a laser plume, comprising a plasma and ablated materials, is often formed above the crater. In some embodiments, the single pulse pattern successfully avoids the laser plume with successive pulses, which are not directed to the same location. The burst pattern may fail to avoid the plume, causing the laser beam to be attenuated by the plume and material removal efficiency to drop.

As discussed above, the single pulse ablation mode generally uses longer pulse widths (e.g., greater than 100 μs) than the pulse widths used in burst-mode ablation, which are typically shorter than 90 μs (e.g., 40-90 μs, 20-40 μs, 2-20 μs). Although a single pulse can ablate and remove a portion of the tissue, a single pulse often does not remove enough material to reach a desired depth and/or cross-sectional area. A single pulse may remove material up to a depth smaller than a desired depth. For example, according to some embodiments a single pulse material removal depth is between 1 and 100 micron. In order to achieve the desired depth (e.g., 0.2 mm, 0.5 mm, 1 mm, or more, it is necessary in some cases to deliver one or more additional pulses to the same spot. In order to form a wider and/or deeper crater than can be formed using a single pulse, in some cases it is necessary to deliver one or more additional pulses to adjacent spots. Repeating delivery of single pulses to the same spot or adjacent spots is different from the burst mode delivery of pulses, because in the burst mode each individual pulse is not designed to cause ablation; instead, a number of pulses collectively cause an ablation. In the single-pulse mode, however, whether the pulses are repeated or not, each pulse is designed to ablate at least some tissue material.

In various instances, patients may be more likely to feel a negative sensation when the burst mode is used with pulse widths greater than 40 μs. In comparison, the same patients who felt discomfort during treatment using the burst mode were able to have the entire procedures done, with generally no discomfort and no anesthesia, using the single pulse mode having pulse widths of 90 μs or longer.

Figure 17:
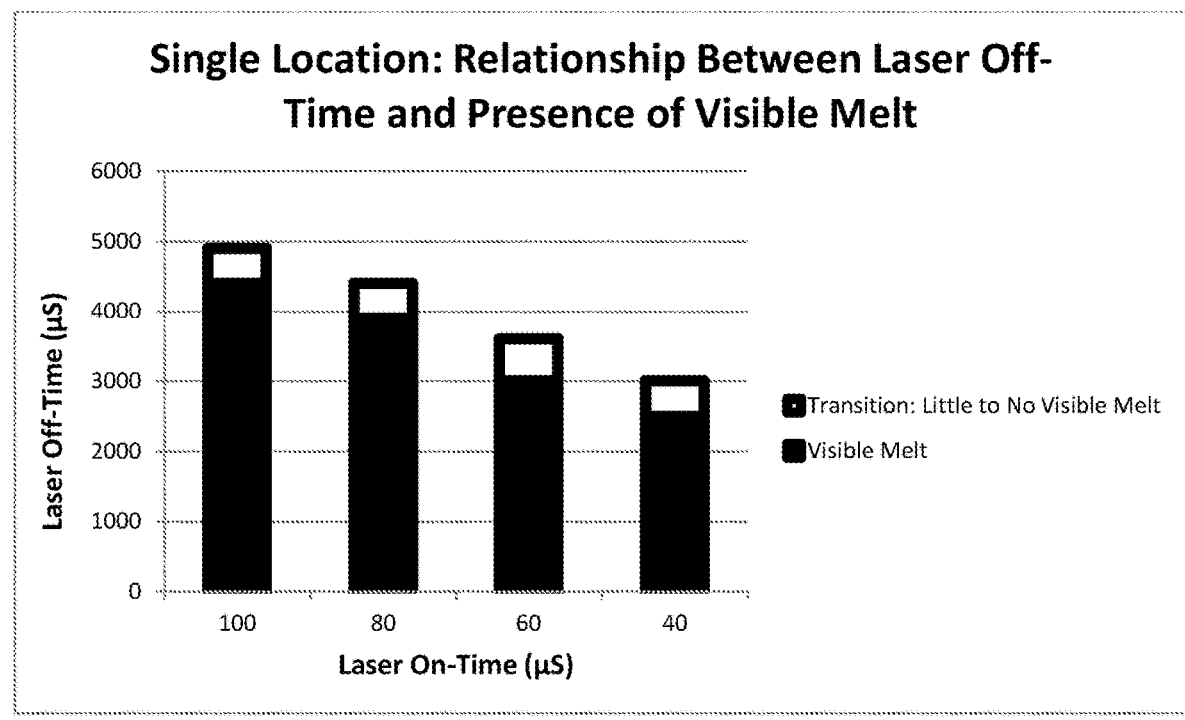
FIG. 17 is a chart showing example data indicating when visible melt appears in a sample as a function of Laser Off-Time, for various Laser On-Times.

As described above, in various embodiments, the time interval between laser pulses or bursts directed to the same or adjacent spots can affect performance. These effects can be further described by examining a laser pattern having only one location. FIG. 17 illustrates the performance of a single location laser pattern containing 1,000 consecutive hits on a human enamel surface. Laser On-Time is shown along the horizontal axis. Laser On-Time as used herein refers to an amount of time the laser is commanded to fire. Commonly, the laser will have a delay that prevents the Laser On-Time from being exactly equal to the duration of the ON time of the corresponding optical pulse. For example, for a repetition rate of 1 KHz or less, the E-150i laser has a delay of about 7.4 μs. Therefore, a 100 μs Laser On-Time generally corresponds to a 92.6 μs optical pulse ON duration.

In FIG. 17, Laser On-Times of 100, 80, 60, and 40 μs are shown to ablate enamel resulting in a significantly melted surface when a Laser Off-Time is less than a transitory range, which is dependent upon the Laser On-Time. The transitory range is defined as a range of Laser Off-Times where little to no visible melt is present during prolonged treatment (e.g., >5 seconds) under magnification of 40×, and any melt that is present is superficial. Treatments having Laser Off-Times greater than the transition range generally exhibited no melt at 40× magnification. From FIG. 17 it can be seen that in some instances, a Laser Off-Time required to prevent melt is dependent, at least in part, upon Laser On-Time (which can be a measure of pulse width and/or pulse energy). For example, the required Laser Off-Time needed to prevent melting is shorter for shorter Laser On-Times.

An individual pulse that can ablate some tissue material can heat some surrounding tissue, though such surrounding tissue material is not ablated. If another pulse is delivered to the same or an adjacent spot (e.g., to deepen and/or widen the cut) before the surrounding tissue material has cooled sufficiently, the other pulse can heat the surrounding tissue further, causing melting or charring thereof. This adverse effect can be avoided or minimized if there is a sufficient time delay between successive pulses delivered to the same or adjacent spots. A time delay that is a multiple (e.g., 2, 5, 10, 20 times, etc.) of the thermal relaxation time of the tissue material can be a sufficient time delay. Another example of the sufficient time delay is the Laser OFF-Time required to prevent melting when pulsing at a single location. In some embodiments, a sufficient time delay is introduced between successive bursts delivered to the same or adjacent spots.

Introducing a sufficient time delay between successive individual pulses or between successive bursts, while beneficial in terms of avoiding or minimizing unwanted tissue melting or charring, can increase the overall treatment time. This can also decrease the efficiency of the system, because the laser source may need to be charged or powered up even though laser pulses are not emitted. In some embodiments, both kinds of negative effects, i.e., unwanted melting/charring and increased treatment time/decreased system efficiency, are avoided or at least minimized by traversing the target spots corresponding to a selected pattern (such as the patterns shown in FIGS. 2C-2E, 5A, 6A, 7A, 8A, and 9A) according to a particular sequence (such as that shown in FIG. 2B).

In the selected sequences, consecutive individual pulses or bursts are not directed to adjacent spots, where abutting (i.e., overlapping, tangential, or spaced apart) craters are formed. For example, with reference to FIG. 2B, if an individual pulse or a burst, denoted pulse/burst "1," is directed to a spot to form the crater 202, the next seven individual pulses or bursts are directed to spots other than the same or adjacent spots where craters 204, 206, 208 are formed. The individual pulse or burst following those additional seven pulses/bursts is denoted pulse/burst "9" and is directed to an adjacent spot, where the crater 208 is formed. Similarly, after pulse/burst "2" is directed to a spot where the crater 210 is formed, the next pulse/burst "3" is not directed to the same or an adjacent spot and, instead is directed to a non-adjacent spot where crater 212 is formed. Thereafter, the pulse/burst "4," which follows the pulse/burst "3," is directed to a spot adjacent to crater 210, where crater 214 is formed.

Thus, if a pair of two pulses/bursts is directed to the same or adjacent spots, at least one pulse/burst intervening the two pulses/bursts is directed to a non-adjacent spot. In various embodiments, the pulse/burst period is greater than a selected multiple of the thermal relaxation time of the material to be ablated. In some embodiments, at least k pulses/bursts are directed to non-adjacent spots where k is greater than one. For example, k can be two, five, seven, ten, etc. In these embodiments, k times the pulse/burst period is greater than a selected multiple of the thermal relaxation time of the material to be ablated. Therefore, these sequences of traversing the target spots allow for sufficient cooling of the tissue surrounding a crater, which can minimize or avoid unwanted charring and melting of the tissue. The one or more intervening pulses/bursts are directed to other locations in the region to be treated, forming craters at those other locations and according to the selected pattern. Therefore, the overall treatment time may not increase substantially (e.g., by more than 1%, 2%, 5%, 10%, 20%, etc.) relative to directing consecutive pulses/burst to the same and/or adjacent spots. This can also minimize or avoid a decrease in treatment efficiency.

In various embodiments, individual laser pulses/bursts can be delivered in a particular sequence, to maintain a minimum interval between a pair of individual pulses/bursts delivered to the same location or to adjacent locations, in order to increase system efficiency, e.g., maximizing the volumetric removal rate of the system, while avoiding/minimizing unwanted charring/melting. Referring again to FIG. 2B, in one embodiment, the Laser ON-Time is approximately 40 μs (i.e., 40 μs with a tolerance of 1%, 2%, 5%, 10%, 20%, etc.). Accordingly, the minimum threshold between individual pulses/bursts directed to the same or adjacent spots is 3.0 ms, with a tolerance of 1%, 3%, 8%, 10%, 20%, etc. in order to prevent or minimize melting. Therefore, a sequence having eight individual pulses/bursts within a 3.0 ms time period, where each pulse/burst is directed to mutually non-adjacent spots, can prevent or minimize melting of the dental enamel, while achieving an overall pulse repetition or burst rate of approximately 2.7 kHz, i.e., 2.7 kHz with a tolerance of 1%, 2%, 5%, 10%, 20%, etc.

In some embodiments, the laser produces an average of 12 mJ per 40 μs ON-Time pulse and, as such, the maximum average power of the laser operating at approximately 2.7 kHz is approximately 32 W. In general, the estimated volumetric removal rate is approximately equal to the average laser power (W) multiplied by enamel volume removed per Joule ($\mu L*10^{-6}/J$). Example data for volume removed per laser energy as a function of Laser Off-Time, is provided in FIG. 19A.

Using the equation with the data for the above example yields: 32 (W)*8.1 ($\mu L*10^{-3}/J$)≈0.260 ($\mu L/S$). Because the threshold interval between intersecting pulses is 3.0 ms, this example pattern will not produce significant melting of the enamel. As used herein, significant melting means melting of more than 0.5%, 1%, 5%, 10%, 12%, 20%, etc., of the enamel volume within a specified distance of the spot to which the laser beam is directed. The specified distance can be on the order of the radius of a crater, e.g., 0.1 mm, 0.15 mm, 0.2 mm, 0.23 mm, 0.25 mm, 0.3 mm, etc. In general, in various embodiments, any number of intervening pulse/burst locations be used (e.g., in a range from 1-10, in a range from 10-20, in a range from 20-50, in a range from 50-100, etc.). In some embodiments the number of intervening pulse/burst locations is related to a number of pulse locations within the pattern. For example, a pattern having about 50 pulse locations will typically have no more than 8-12 intervening pulses between each adjacent pulse locations in the pattern. A pattern having about 25 pulse locations will typically have no more than 4-6 intervening pulses between each adjacent pulse locations in the pattern. And, a pattern having about 12 pulse locations will typically have no more than 2-3 intervening pulses between each adjacent pulse locations in the pattern. In some embodiments, the number of non-adjacent target locations is selected such that the time between all pairs of two adjacent locations is maximized. In some cases, the average time between all pairs of two adjacent locations is maximized.

Figure 18A:
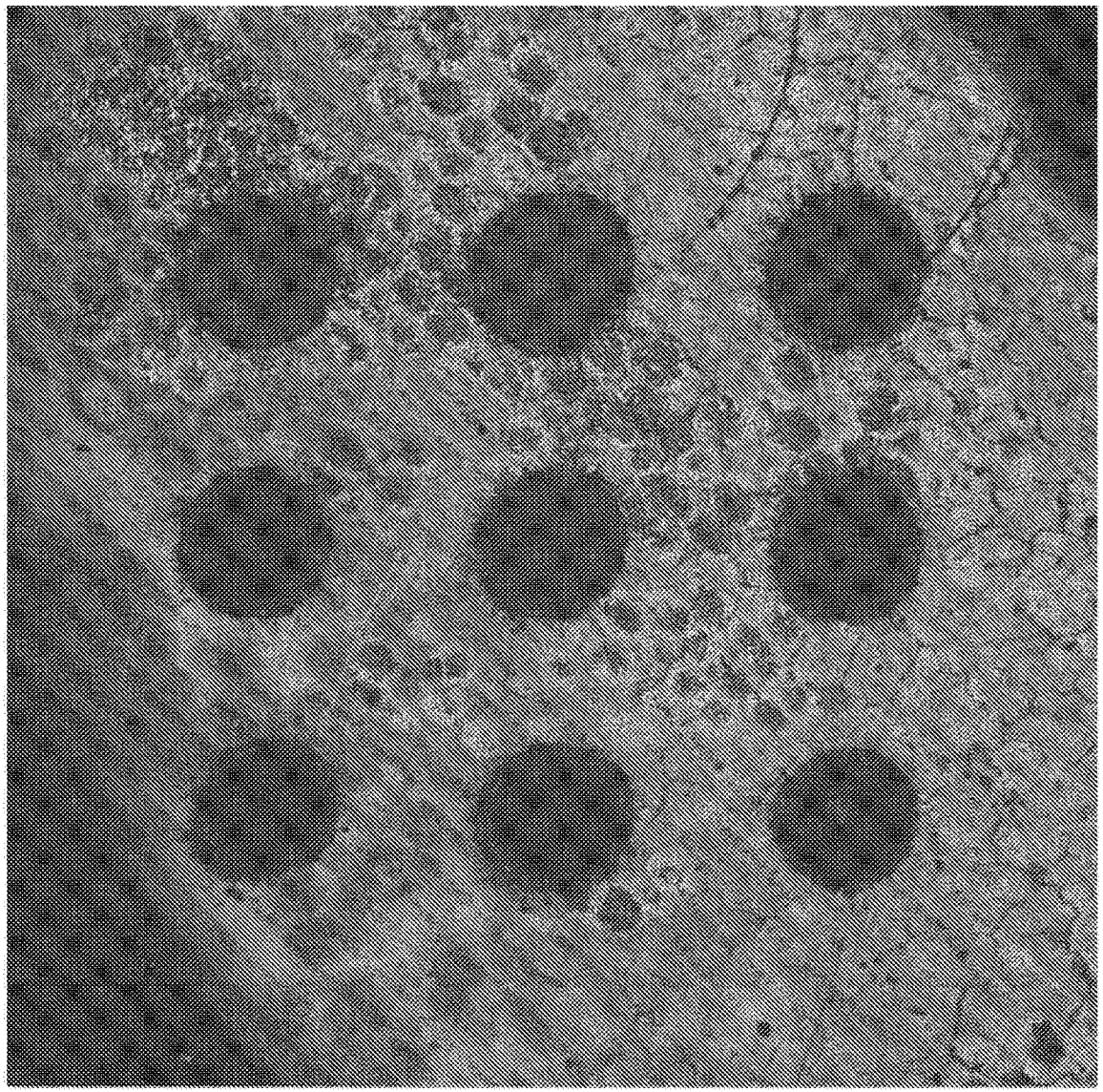
FIGS. 18A-18C are confocal microscope images of craters formed by various numbers of laser pulses, at various Laser Off-Times, according to various embodiments.
Figure 18B:
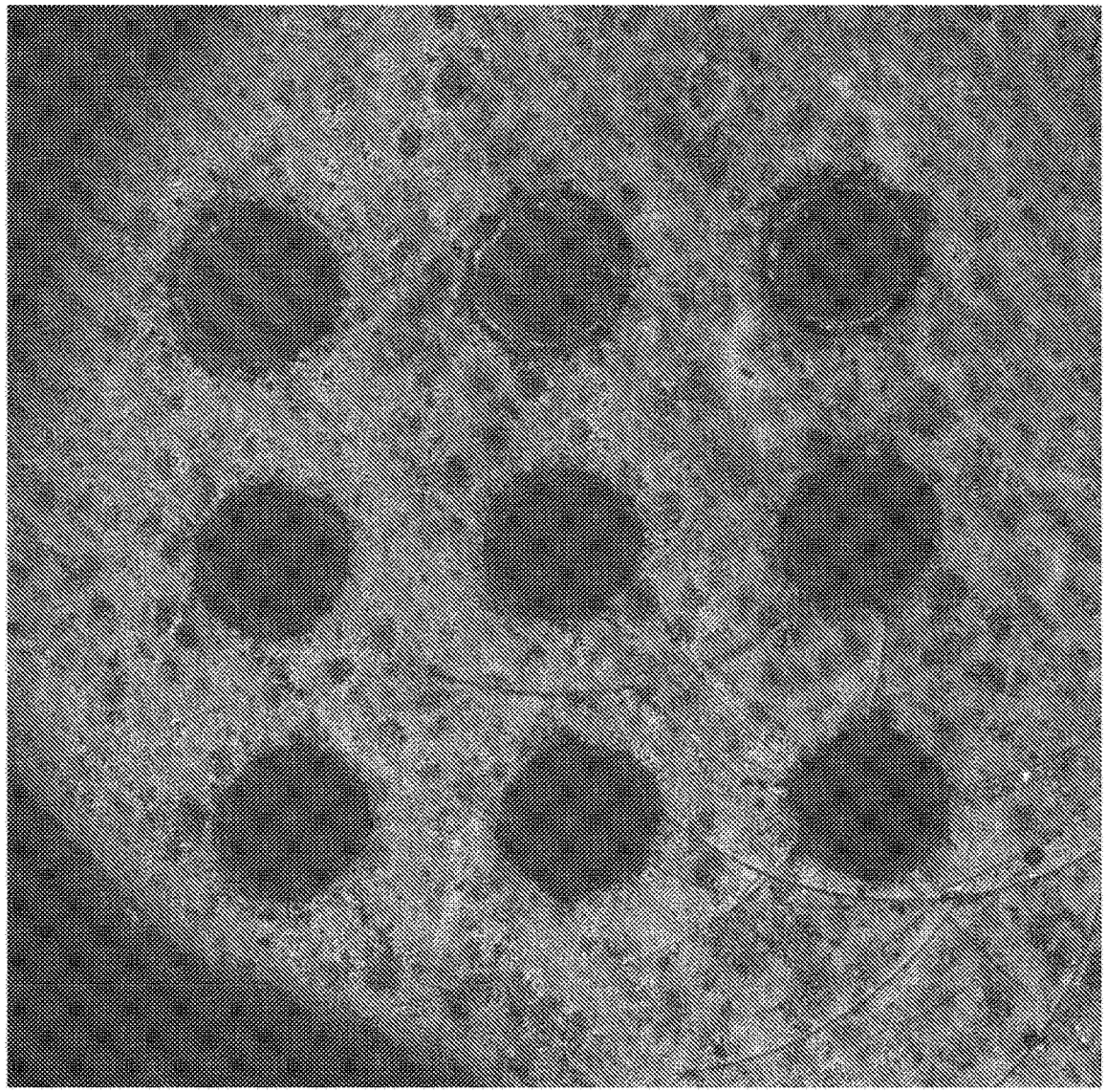
Figure 18C:
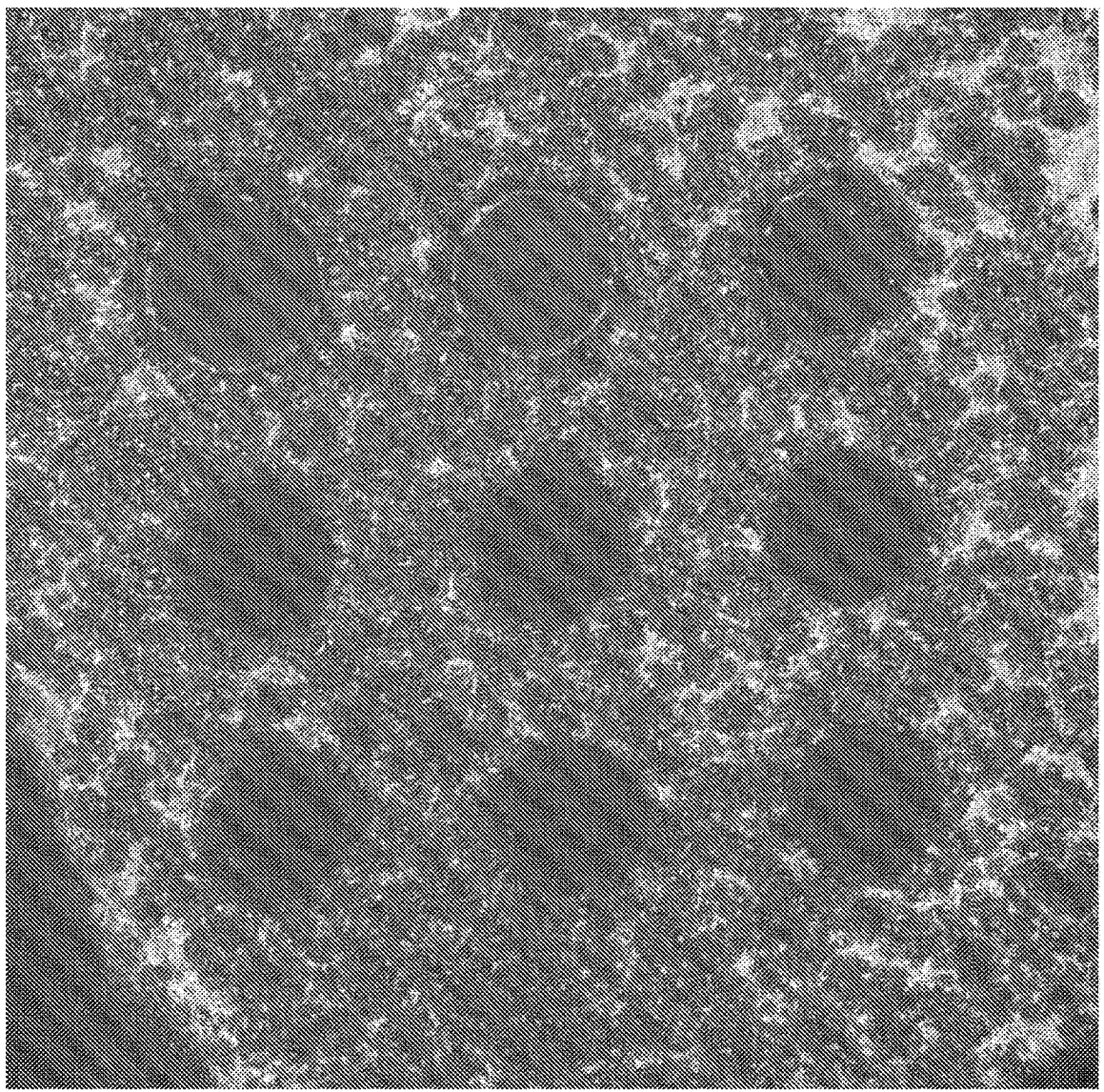

FIG. 18A depicts images of human molars taken by a confocal microscope showing nine craters each formed by directing 10 laser pulses to a single location. FIG. 18B shows nine craters, each formed by directing 20 pulses to a single location, and FIG. 18C shows nine craters, each formed by directing 30 pulses to a single location. In each of the 27 cases, the ON duration of each laser pulse is 40 μs. For each crater in FIG. 18A, the table in FIG. 18A shows the respective Laser Off-Time. FIGS. 18B and 18C each includes a table that shows the Laser Off Times for the different craters depicted in the respective figures. The human molars shown in 18A-C were ground flat and parallel with the image plane. Very little to no melt is present in any of the 10 pulse craters in FIG. 18A. Melt is visible at Laser OFF-Times of 500, 1,500, and 2,000 μs in the 20 and 30 pulse craters in FIGS. 18B-C. As described above and depicted in FIG. 17, melt was slightly visible at 2,500 μs Laser OFF-Time during prolonged irradiation (e.g., 1,000 or more consecutive 40 μs pulses).

Figure 19A:
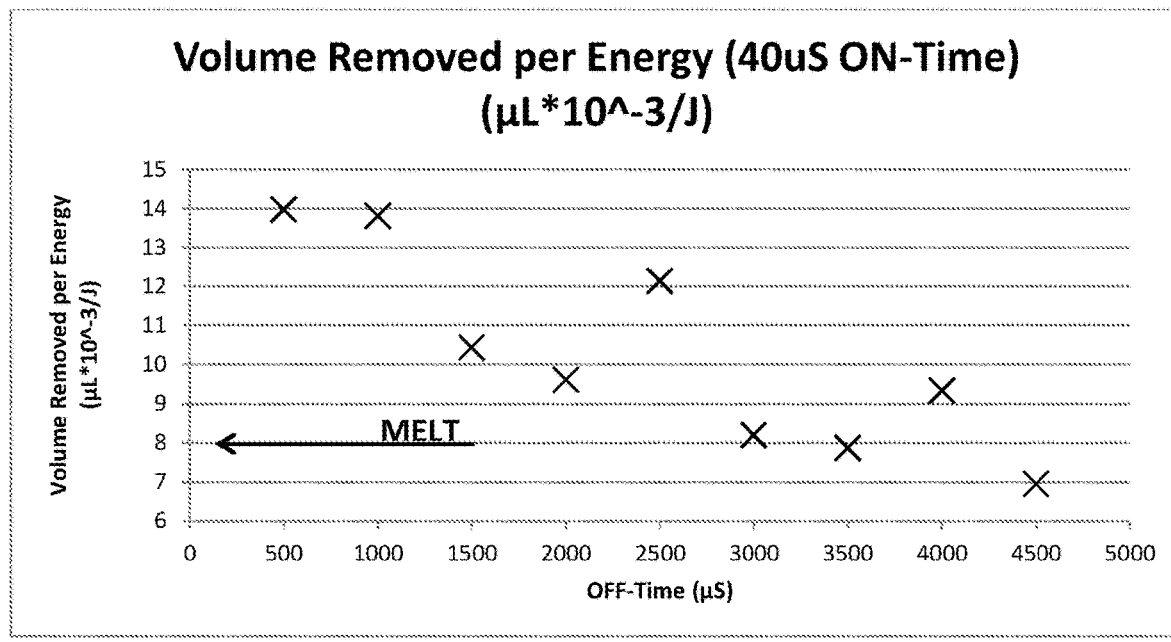
FIGS. 19A-19B are graphs showing example data for volume removed per unit energy as a function of laser off-time, according to various embodiments.
Figure 19B:
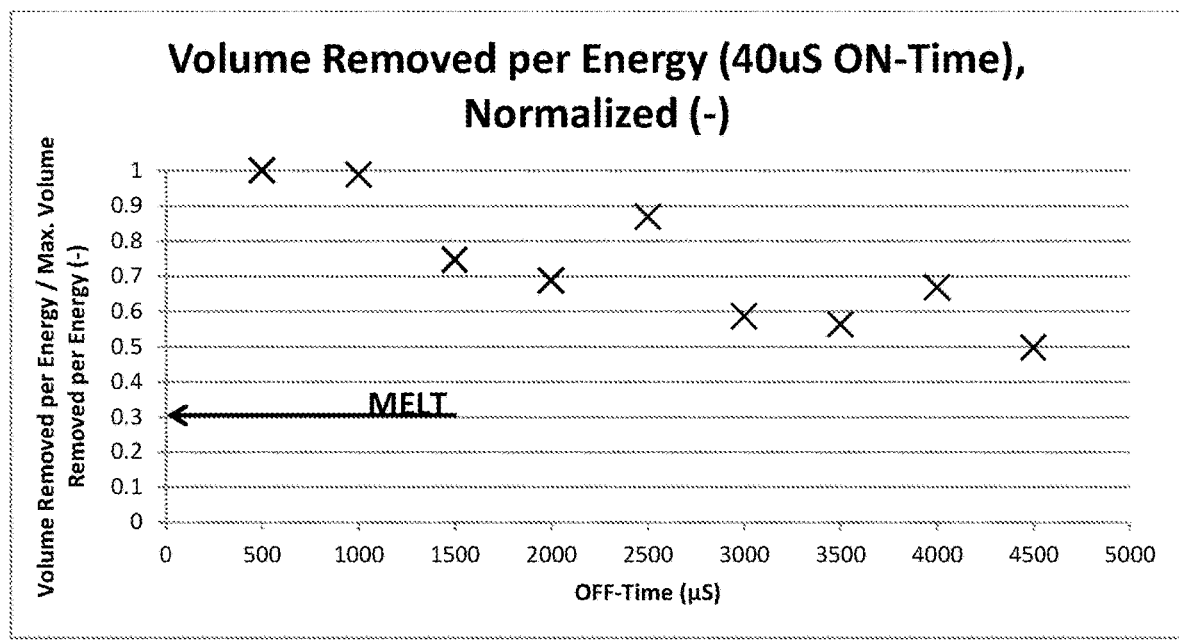

Volume measurements of the 30 pulse craters shown in FIG. 18C were derived from confocal microscope images of each crater. Graphs showing the volume of enamel removed as a function of Laser OFF-Time are shown in FIGS. 19A-B. Volume removed per Joule can provide a measure of the ablation efficiency and, for a given energy per pulse and a given pulse ON duration, the total laser energy delivered to the material to be treated in a unit amount of time can be varied by varying the Laser OFF-Time.

In some cases, some residual heat in the tissue to be ablated may actually help ablation thereof, if the next pulse is delivered before the material cools off completely. If this is correct, a shorter OFF time may require fewer pulses, i.e., less energy, to ablate a certain amount of material relative to a longer OFF time. In that case, the volume/energy ratio would increase as the OFF time decreases. This would begin to change when the residual heat in the surrounding tissue begins to cause melting. For example, with reference to FIG. 19A, there is melting at OFF time 1.5 ms and no melting at 2.0 ms. But, at OFF time 2.0 ms fewer pulses (and, hence, less energy) would be required to ablate μ mL of material than the number of pulses (and energy) required to ablate the same amount when the OFF time is 2.5 ms, 3 ms, etc.

Referring to FIG. 19A, shorter Laser OFF-Times generally result in greater volume removed per unit energy. In some cases, the Laser OFF-time that results in the largest volume removed per unit energy ratio also corresponds to the largest amount of melting of tissue surrounding the ablated crater. Therefore, the Laser OFF-time may be selected so as to maximize ablation efficiency while minimizing or avoiding unwanted melting of some material. As an example, FIG. 19B shows that Laser OFF-Times expected to produce no significant melting during prolonged laser irradiation at a single location (e.g., >2.5 ms) correspond to approximately 60% of a maximum volume removed per unit energy for the same Laser ON-Time.

It should be understood that the OFF time is a convenient measure when individual pulses or bursts are delivered to only one spot. Therefore, this OFF time is referred to herein as single-location OFF time. In some embodiments, after delivering one pulse/burst to a selected spot one or more intervening pulses or bursts are delivered to one or more spots that are not adjacent to the selected spot, before delivering another pulse/burst to the selected spot. In these embodiments, the OFF time of a pulse or a burst can be less than the single-location OFF time. Instead, in these embodiments, the duration of the one or more intervening pulses/bursts should at least be equal to the single-location OFF time.

Figure 20:
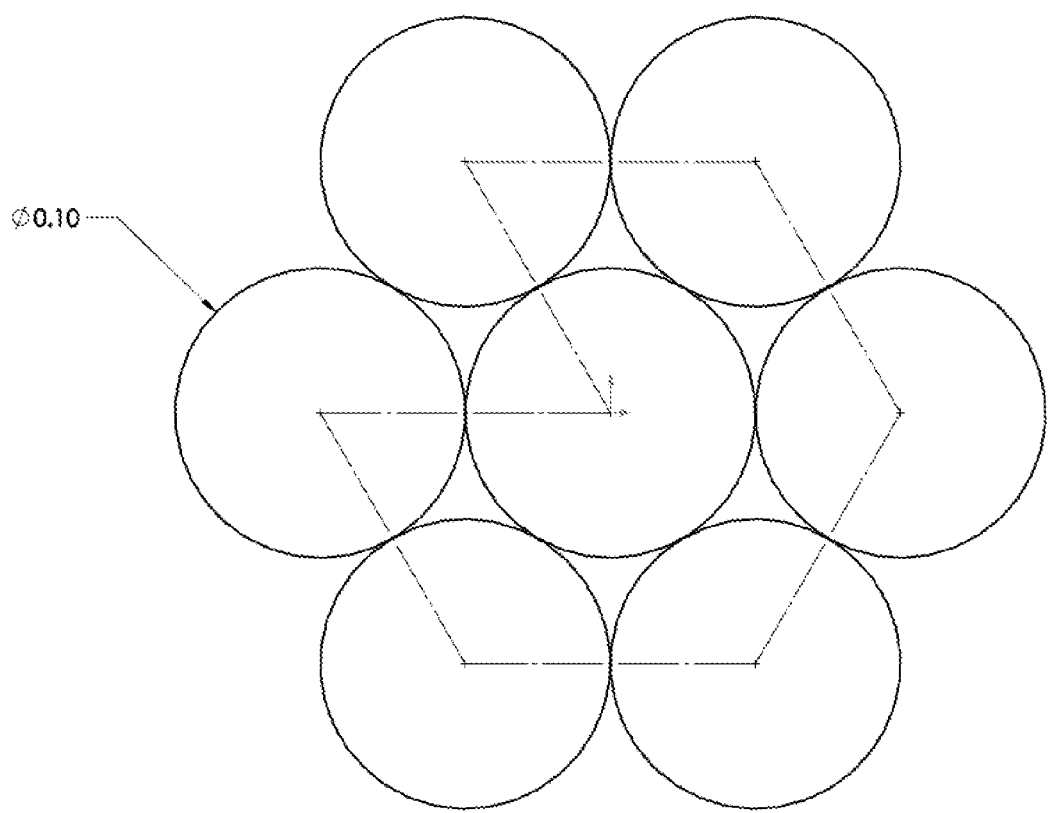
FIG. 20 depicts an example pattern used to illustrate an effect of spacing on cooling interval, according to various embodiments.

As described above, tissue in and about the ablated crater is heated after a laser pulse is delivered. In order to prevent recast melting and other unwanted surface effects, it is important to wait for an interval of time before ablating the same location again. Areas surrounding the crater will also be heated and will require a cooling interval prior to ablation of an adjacent location, in order to prevent surface modification. An example pattern shown in FIG. 20 is used to illustrate the effects of spacing on cooling interval. FIG. 20 shows a seven point pattern arranged in a hexagonal circle packing arrangement. The spacing between neighboring points is shown to be 0.1 mm; however, this parameter can be varied (as described below). The dotted line in FIG. 20 illustrates the path the beam guidance system takes as the laser traverses these seven locations. The sequence of the points in this example illustrative pattern is such that each laser pulse is directed to a location that is adjacent to the preceding location.

The pattern shown in FIG. 20 was used to ablate extracted human molar. Spacing between neighboring pulse locations was varied from 0.1 mm to 0.3 mm, and Laser ON-Time was varied from 40 μs to 120 μs. The pattern was repeated about 1,000 times during ablation. At each combination of spacing and Laser ON-Time the amount of time between neighboring pulses was modified until ablation occurred without melt visibly present. The results are shown in FIGS. 21A-21B.

Figure 21A:
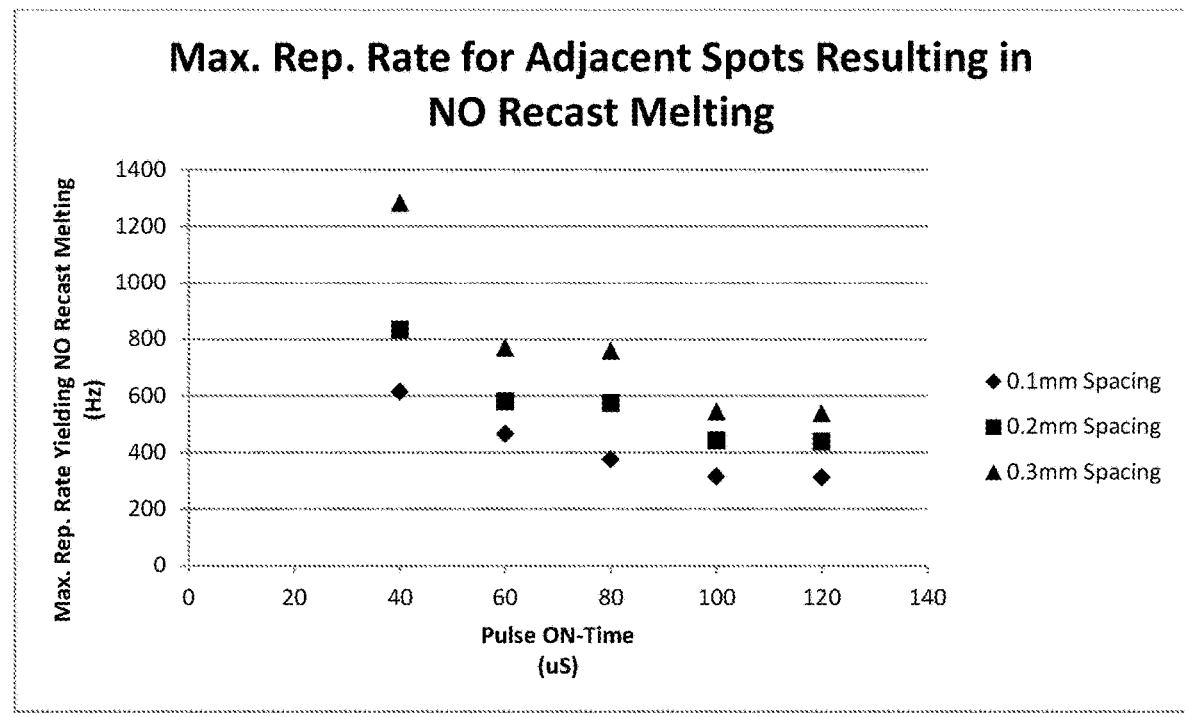
FIG. 21A is a graph showing example data for a maximum repetition rate yielding no recast melting as a function of Laser On-Time, for various pattern spacings.
Figure 21B:
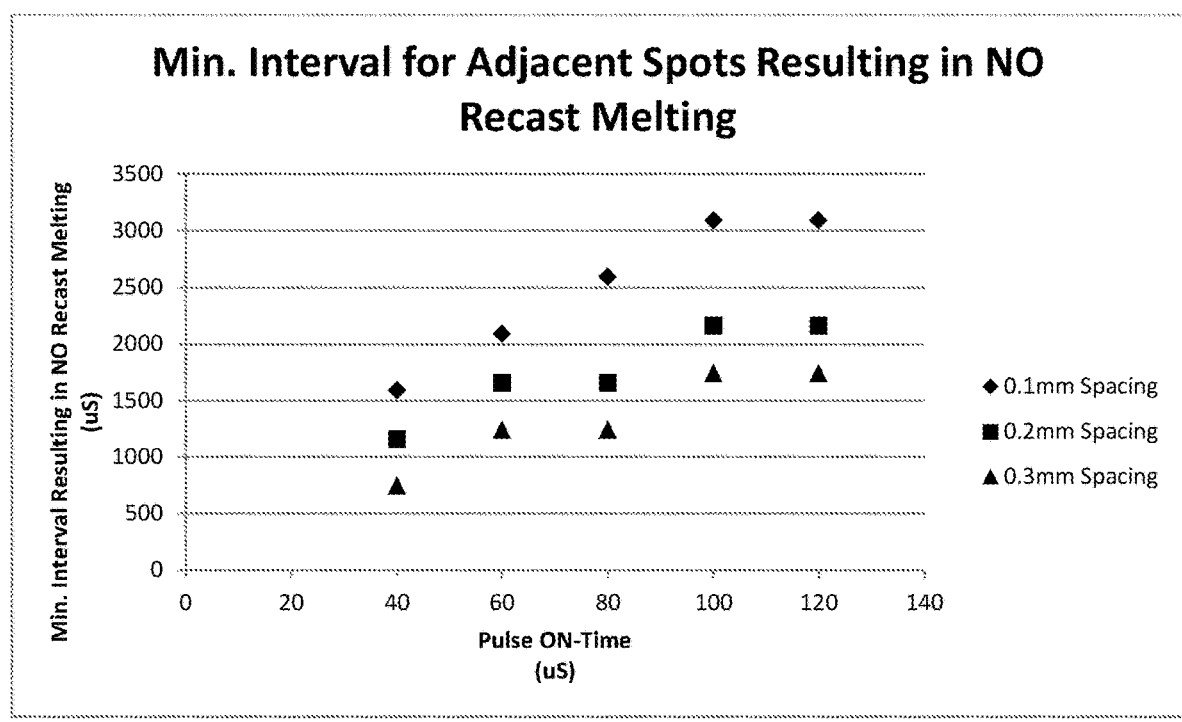
FIG. 21B is a graph showing example data for minimum interval yielding no recast melting as a function of Laser On-Time, for various pattern spacings.

Referring to FIG. 21A, the interval between directing laser pulses/bursts to adjacent locations that was determined to prevent melting is shown to be a function of both spacing between the locations and Laser ON-Time. In general, pulse target locations spaced farther apart require less time between successive pulses/bursts, whereas adjacent locations that are nearer to each other require more time between successive pulses/bursts. It can be seen that greater spacing allows the laser to fire at higher repetition rates without causing melting. FIG. 21B illustrates the same results as FIG. 21A, but instead of showing maximum laser pulse repetition rate, the data shows the minimum interval between pulses that is achievable, without melt visibly present. Both FIG. 21A and FIG. 21B show that longer Laser ON-Times require greater intervals between pulses acting on abutting locations, in order to prevent melting. In addition to affecting the melting threshold, modifying pattern geometry and sequence according to the present disclosure positively affected the sensation felt by patients during treatment.

As referred to above, a benefit of laser dental treatment is that for many procedures local anesthesia is not required. It was found that increasing time and distance between sequential and adjacent pulse locations also aides in reducing sensation in patients. For dental laser treatment sensation a 0-10 discomfort scale is used, where: 0=No Sensation, 1-3=Cold or Blowing Air Sensation, 3-5=Slight Discomfort, 6-8=Discomfort, and 8-10=Painful. A baseline value of 2.17 on average was found with patterns having sequences similar to those described in FIGS. 5A, 6A, 7A, 8A, and 9A. When patterns having a sequence more like that described in FIG. 2B were employed the average sensation value dropped to 0.92. Sequence was therefore found to affect patient sensation positively when modified to increase the amount of time between nearby pulse locations. The selection of laser parameters according to this disclosure therefore will help to address the pain and fear, which for years have been a natural concomitant of dental visits.

It should be understood that the OFF time is a convenient measure when individual pulses or bursts are delivered to only one spot. Therefore, this OFF time is referred to herein as single-location OFF time. In some embodiments, after delivering one pulse/burst to a selected port one or more intervening pulses or bursts are delivered to one or more spots that are not adjacent to the selected spot, before delivering another pulse/burst to the selected spot. In these embodiments, the OFF time of a pulse or a burst can be less than the single-location OFF time. Instead, in these embodiments, the duration of the one or more intervening pulses/bursts should at least be equal to the single-location OFF time.

A benefit of single pulse patterns compared to conventional patterns is that one parameter, burst pulse frequency, is eliminated. In single pulse patterns, the repetition rate of pulses within the laser burst no longer needs to be set or controlled by the operator (e.g., dentist).

Furthermore, once the minimum threshold time between intersecting pulses is defined, this parameter can be hard coded or rendered inaccessible, since the operator does not need to set or modify this parameter during use. Thus, a single pulse laser pattern may be controlled by the operator by simply modulating one parameter (e.g., pulse width). In some embodiments modulation of pulse width may be done through a variable input device (e.g., a foot pedal) providing an intuitive and effective user experience.

In various embodiments, the laser beams that deliver the patterns described herein can be defined, at least in part, by their fluence. Fluence is a useful measure of energy density and can be defined as an amount of energy per pulse divided by the cross-sectional laser beam area at focus. In multi-pulse situations, an average pulse energy is often used. Average pulse energy may be measured directly by a laser energy meter. Additionally, it is advantageous in some situations to derive average pulse energy from average laser power and average laser repetition rate. The average energy per pulse is equal to the average laser power divided by the average repetition rate. Area of a laser beam at focus is dependent upon the beam width of the laser beam at focus (or waist). Lasers beams have an energy profile that describes the amount of energy across the cross-section of the laser beam. Some energy profiles, such as a top-hat profile, have very steep drops in energy at the edges of the laser beam, which provide a clear demarcation for beam width measurements. However, most laser beams have an energy profile with a Gaussian or near-Gaussian shape. To measure beam width in non-top-hat beams, various techniques or standards are used for consistency. These techniques include: full width at half maximum (FWHM), $1/e^2$ width, D4σ or second moment width, knife edge width such as 90/10, and D86 width, all of which are techniques known by those skilled in the art.

In some instances, the experiments and patterns described herein used a single focused spot size. For some of the experiments and patterns, the size of the focused spot was measured to be about 0.25 mm using the 90/10 knife edge method. Assuming that the focused spot size was Gaussian, these spots can be said to have a $1/e^2$ width of about 0.39 mm.

The terms and expressions employed herein are used as terms and expressions of description and not of limitation and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and operational functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A method for removing a region of dental tissue, the method comprising:
   directing a single laser pulse of a laser beam to each respective tissue location in a pattern of tissue locations within the region of dental tissue to form a plurality of abutting craters, wherein:
      the pattern is a function of crater size and a desired smoothness of the plurality of abutting craters determined based at least in part on a width of the laser beam, energy per pulse of the laser beam, and a characteristic of the tissue, wherein the crater size is a function of a desired ablation efficiency; and
      the abutting craters comprise at least one of: (i) a pair of partially overlapping craters, (ii) a pair of tangent craters, and (iii) a pair of spaced craters separated up to a specified maximum distance.

2. The method of claim 1, wherein at least one of (i) an amount of overlap between partially overlapping craters and (ii) the specified maximum distance is a function of the desired smoothness of the plurality of abutting craters.

3. The method of claim 1, wherein the abutting craters further comprise at least one of: (i) three partially overlapping craters, (ii) three tangent craters, and (iii) three spaced craters separated up to a specified maximum distance.

4. The method of claim 1, wherein the ablation efficiency is a function of a volume of the plurality of abutting craters and a total energy of the laser beam directed to the pattern of tissue locations.

5. The method of claim 1, wherein the desired ablation efficiency is at least 50 percent of a theoretical maximum ablation efficiency.

6. The method of claim 1, wherein the step of directing a single laser pulse to each respective tissue location comprises:
   directing a first single laser pulse to a first tissue location to form a first crater; and
   directing a next single laser pulse to a second tissue location to form a second crater not abutting the first crater.

* * * * *